(12) United States Patent
Kuebler et al.

(10) Patent No.: US 8,801,666 B2
(45) Date of Patent: Aug. 12, 2014

(54) DEVICE FOR REDUCING PRESSURE VARIATIONS IN AN ASPIRATION BRANCH, AND SURGICAL SYSTEM

(75) Inventors: Christoph Kuebler, Oberkochen (DE); Martin Kraus, Huettlingen (DE); Michael Eichler, Aalen (DE); Tobias Maier, Stuggart (DE)

(73) Assignee: Carl Zeiss Meditec AG, Jena (DE)

( * ) Notice: Subject to any disclaimer, the term of this patent is extended or adjusted under 35 U.S.C. 154(b) by 391 days.

(21) Appl. No.: 12/666,007

(22) PCT Filed: Jun. 18, 2008

(86) PCT No.: PCT/EP2008/057717

§ 371 (c)(1),
(2), (4) Date: Apr. 2, 2010

(87) PCT Pub. No.: WO2009/007212

PCT Pub. Date: Jan. 15, 2009

(65) Prior Publication Data

US 2011/0178457 A1    Jul. 21, 2011

(30) Foreign Application Priority Data

Jul. 6, 2007    (DE) .......................... 10 2007 031 722

(51) Int. Cl.
*A61B 17/20*    (2006.01)
*A61M 1/00*    (2006.01)
*A61F 9/007*    (2006.01)

(52) U.S. Cl.
CPC .................................. *A61M 1/0031* (2013.01); *A61F 9/00745* (2013.01)
USPC ................. 604/118; 604/22; 604/30; 604/31; 604/32; 604/33; 604/34; 604/35; 604/119; 604/120

(58) Field of Classification Search
USPC .................. 604/22, 30–34, 35, 118–120, 246
See application file for complete search history.

(56) References Cited

U.S. PATENT DOCUMENTS

| 2,754,968 | A | * | 7/1956 | Hage et al. ..................... 209/729 |
| 4,182,385 | A | | 1/1980 | Williamson |
| 5,441,482 | A | * | 8/1995 | Clague et al. .................... 604/35 |
| 5,766,276 | A | * | 6/1998 | Javet et al. .................... 48/198.7 |
| 6,599,271 | B1 | * | 7/2003 | Easley .......................... 604/119 |
| 6,945,969 | B1 | * | 9/2005 | Morris et al. ................. 604/508 |
| 8,142,653 | B2 | * | 3/2012 | Beden et al. .................. 210/240 |

FOREIGN PATENT DOCUMENTS

| DE | 35 01 655 C1 | 5/1986 |
| WO | WO 89/03230 | 4/1989 |
| WO | WO 03101510 A1 * | 12/2003 |

OTHER PUBLICATIONS

Fox et al. Intoduction to Fluid Mechanics, 1985, John Wiley and Sons, Inc., Third Edition, p. 367-368.*

* cited by examiner

*Primary Examiner* — Emily Schmidt
*Assistant Examiner* — Lauren M Peng
(74) *Attorney, Agent, or Firm* — Fish & Richardson P.C.

(57) ABSTRACT

The invention relates to a device for reducing pressure variations in a fluid flowing in an aspiration branch of a surgical system, which pressure variations are generated by a pump that delivers in a non-continuous manner in the active operating state, with a diffuser arrangement which is arranged, in the aspiration branch, upstream of the pump in the direction of flow of the fluid. The invention also relates to a surgical system, in particular an ophthalmic microsurgical system for lens surgery.

17 Claims, 18 Drawing Sheets

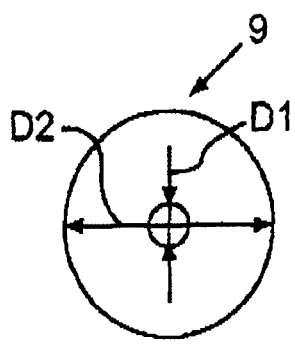
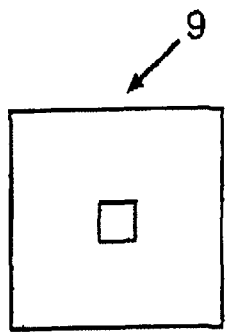
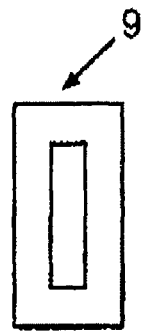
Fig.5a  Fig.5b  Fig.5c
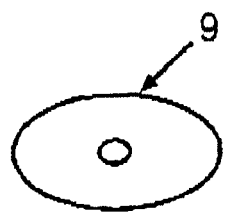
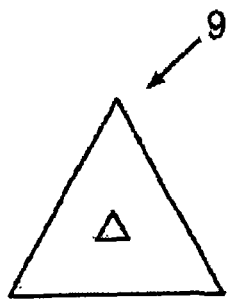
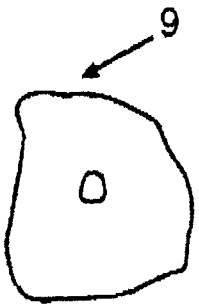
Fig.5d  Fig.5e  Fig.5f
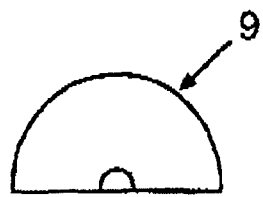
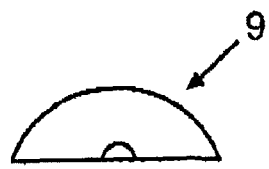
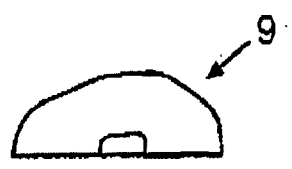
Fig.5g  Fig.5h  Fig.5i
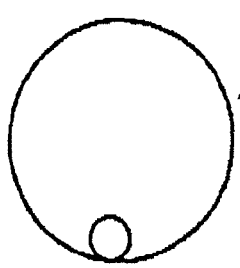
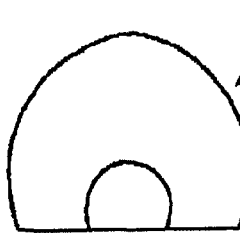
Fig.5j  Fig.5k

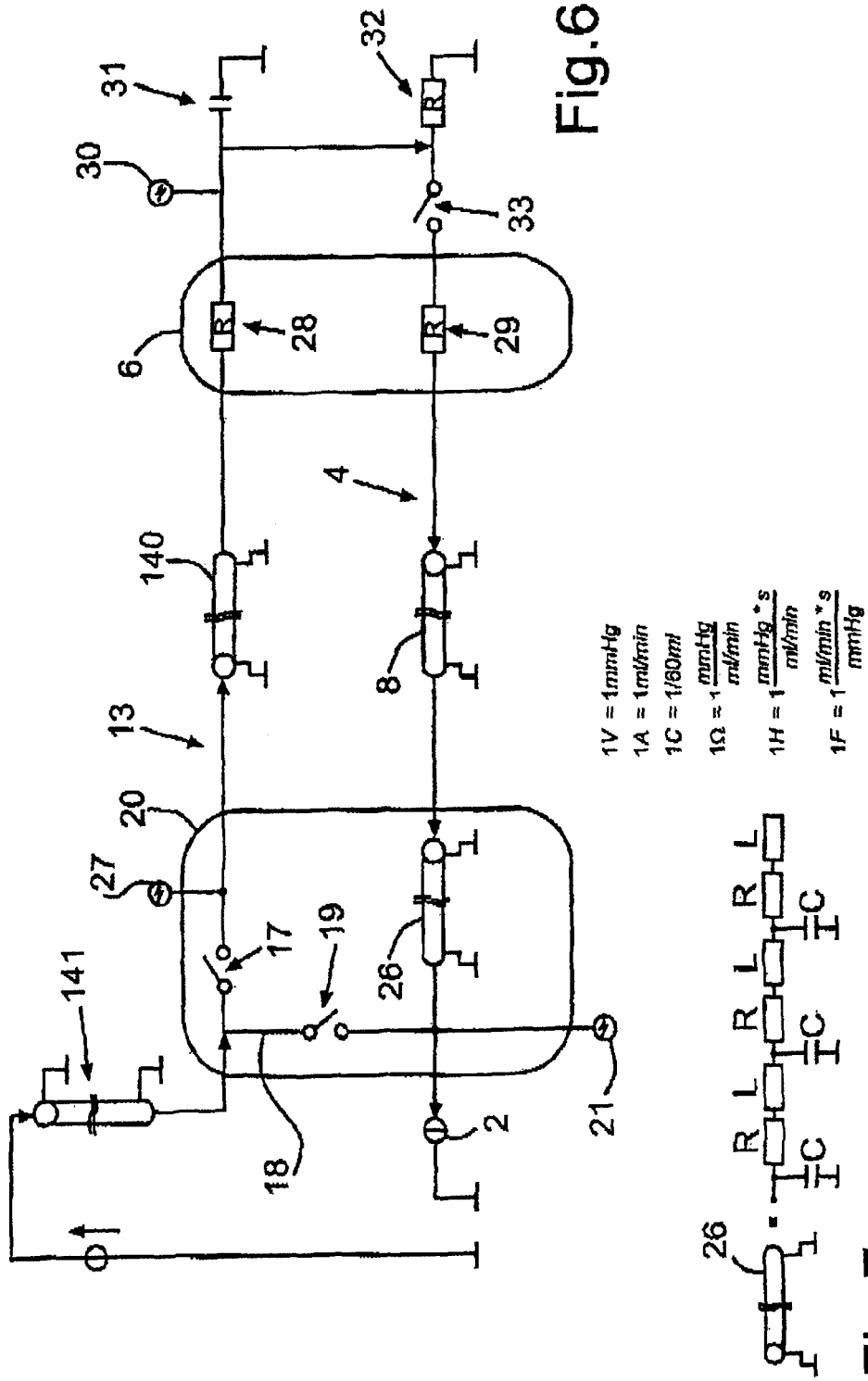

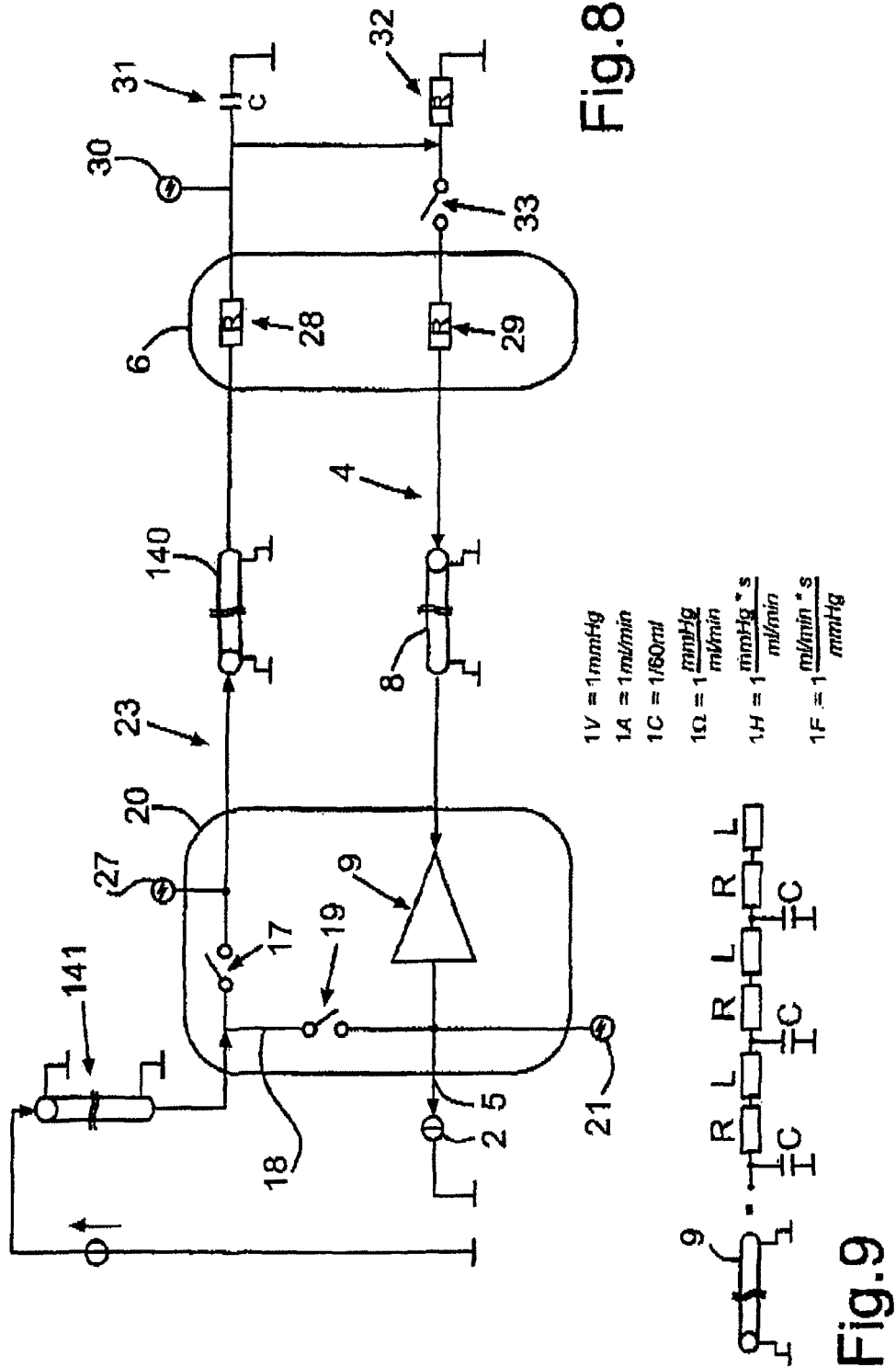

| Element | Length | Internal diameter | Wall thickness H | Young's modulus | Poisson number | Hydr. resistance | Hydr. inductance | Hydr. Capacitance | Wave speed |
|---|---|---|---|---|---|---|---|---|---|
| | m | mm | mm | MPa | | mmHg/ml'min | mmHg*s/(ml/min) | ml/min*s/mmHg | m/sec |
| BSS Tube | 2.000 | 3.200 | 0.800 | 1 | 0.30 | 0.0973 | 0.0311 | 0.5147 | 15.8 |
| IRR Tube | 2.000 | 4.000 | 0.800 | 1 | 0.30 | 0.0399 | 0.0199 | 1.0053 | 14.1 |
| IRR Handpiece | 0.100 | 1.000 | 0.300 | | | 0.5103 | | | |
| ASP Handpiece | 0.060 | 0.800 | 0.300 | | | 0.7475 | | | |
| EYE R | | | | | | 6.3789 | | | |
| EYE C | | | | | | | | 0.0500 | |
| ASP Tube | 2.000 | 1.800 | 1.000 | 3 | 0.30 | 0.9722 | 0.0982 | 0.0244 | 40.8 |
| ASP Line | 0.100 | 1.800 | 1.000 | 2000 | 0.30 | 0.0486 | 0.0049 | 0.0000 | 1054.1 |
| K=1 | | | | | | | | | |
| DIFF1 | 0.010 | 1.800 | 1.000 | 2000 | 0.30 | 0.0049 | 4.912e-004 | 1.8322e-007 | 1054.1 |
| DIFF2 | 0.010 | 1.800 | 1.000 | 2000 | 0.30 | 0.0049 | 4.912e-004 | 1.8322e-007 | 1054.1 |
| DIFF3 | 0.010 | 1.800 | 1.000 | 2000 | 0.30 | 0.0049 | 4.912e-004 | 1.8322e-007 | 1054.1 |
| DIFF4 | 0.010 | 1.800 | 1.000 | 2000 | 0.30 | 0.0049 | 4.912e-004 | 1.8322e-007 | 1054.1 |
| DIFF5 | 0.010 | 1.800 | 1.000 | 2000 | 0.30 | 0.0049 | 4.912e-004 | 1.8322e-007 | 1054.1 |
| DIFF6 | 0.010 | 1.800 | 1.000 | 2000 | 0.30 | 0.0049 | 4.912e-004 | 1.8322e-007 | 1054.1 |
| DIFF7 | 0.010 | 1.800 | 1.000 | 2000 | 0.30 | 0.0049 | 4.912e-004 | 1.8322e-007 | 1054.1 |
| DIFF8 | 0.010 | 1.800 | 1.000 | 2000 | 0.30 | 0.0049 | 4.912e-004 | 1.8322e-007 | 1054.1 |
| DIFF9 | 0.010 | 1.800 | 1.000 | 2000 | 0.30 | 0.0049 | 4.912e-004 | 1.8322e-007 | 1054.1 |
| DIFF10 | 0.010 | 1.800 | 1.000 | 2000 | 0.30 | 0.0049 | 4.912e-004 | 1.8322e-007 | 1054.1 |

Fig.16

| Element | Length | Internal diameter | Wall thickness H | Young's modulus | Poisson number | Hydr. resistance | Hydr. inductance | Hydr. Capacitance | Wave speed |
|---|---|---|---|---|---|---|---|---|---|
| | m | mm | mm | MPa | | mmHg/ml*min | mmHg*s/ (ml/min) | ml/min*s/mmHg | m/sec |
| BSS Tube | 2.000 | 3.200 | 0.800 | 1 | 0.30 | 0.0973 | 0.0311 | 0.5147 | 15.8 |
| IRR Tube | 2.000 | 4.000 | 0.800 | 1 | 0.30 | 0.0399 | 0.0199 | 1.0053 | 14.1 |
| IRR Handpiece | 0.100 | 1.000 | 0.300 | | | 0.5103 | | | |
| ASP Handpiece | 0.060 | 0.800 | 0.300 | | | 0.7475 | | | |
| EYE R | | | | | | 6.3789 | | | |
| EYE C | | | | | | | | 0.0500 | |
| ASP Tube | 2.000 | 1.800 | 1.000 | 3 | 0.30 | 0.9722 | 0.0982 | 0.0244 | 40.8 |
| ASP Line | 0.100 | 1.800 | 1.000 | 2000 | 0.30 | 0.0486 | 0.0049 | 0.0000 | 1054.1 |
| K=15 | | | | | | | | | |
| DIFF1 | 0.010 | 1.800 | 1.000 | 2000 | 0.30 | 0.0049 | 4.912e-004 | 1.8322e-007 | 1054.1 |
| DIFF2 | 0.010 | 4.600 | 1.000 | 2000 | 0.30 | 0.0001 | 7.522e-005 | 3.0579e-006 | 659.4 |
| DIFF3 | 0.010 | 7.400 | 1.000 | 2000 | 0.30 | 0.0000 | 2.906e-005 | 1.2730e-005 | 518.9 |
| DIFF4 | 0.010 | 10.200 | 1.000 | 2000 | 0.30 | 0.0000 | 1.530e-005 | 3.3339e-005 | 442.8 |
| DIFF5 | 0.010 | 13.000 | 1.000 | 2000 | 0.30 | 0.0000 | 9.417e-006 | 6.9021e-005 | 392.2 |
| DIFF6 | 0.010 | 15.800 | 1.000 | 2000 | 0.30 | 0.0000 | 6.375e-006 | 1.2391e-004 | 355.8 |
| DIFF7 | 0.010 | 18.600 | 1.000 | 2000 | 0.30 | 0.0000 | 4.600e-006 | 2.0216e-004 | 327.9 |
| DIFF8 | 0.010 | 21.400 | 1.000 | 2000 | 0.30 | 0.0000 | 3.475e-006 | 3.0789e-004 | 305.7 |
| DIFF9 | 0.010 | 24.200 | 1.000 | 2000 | 0.30 | 0.0000 | 2.718e-006 | 4.4524e-004 | 287.5 |
| DIFF10 | 0.010 | 27.000 | 1.000 | 2000 | 0.30 | 0.0000 | 2.183e-006 | 6.1839e-004 | 272.2 |

Fig.17

| Element | Length | Internal diameter | Wall thickness H | Young's modulus | Poisson number | Hydr. resistance | Hydr. inductance | Hydr. Capacitance | Wave speed |
|---|---|---|---|---|---|---|---|---|---|
| | m | mm | mm | MPa | | mmHg/ml*min | mmHg*s/ (ml/min) | ml/min*s/mmHg | m/sec |
| BSS Tube | 2.000 | 3.200 | 0.800 | 1 | 0.30 | 0.0973 | 0.0311 | 0.5147 | 15.8 |
| IRR Tube | 2.000 | 4.000 | 0.800 | 1 | 0.30 | 0.0399 | 0.0199 | 1.0053 | 14.1 |
| IRR Handpiece | 0.100 | 1.000 | 0.300 | | | 0.5103 | | | |
| ASP Handpiece | 0.060 | 0.800 | 0.300 | | | 0.7475 | | | |
| EYE R | | | | | | 6.3789 | | 0.0500 | |
| EYE C | | | | | | | | 0.0244 | |
| ASP Tube | 2.000 | 1.800 | 1.000 | 3 | 0.30 | 0.9722 | 0.0982 | | 40.8 |
| ASP Line | 0.100 | 1.800 | 1.000 | 2000 | 0.30 | 0.0486 | 0.0049 | 0.0000 | 1054.1 |
| K=20 | | | | | | | | | |
| DIFF1 | 0.010 | 1.800 | 1.000 | 2000 | 0.30 | 0.0049 | 4.912e-004 | 1.8322e-007 | 1054.1 |
| DIFF2 | 0.010 | 5.600 | 1.000 | 2000 | 0.30 | 0.0001 | 5.075e-005 | 5.5171e-006 | 587.6 |
| DIFF3 | 0.010 | 9.400 | 1.000 | 2000 | 0.30 | 0.0000 | 1.801e-005 | 2.6094e-005 | 461.3 |
| DIFF4 | 0.010 | 13.200 | 1.000 | 2000 | 0.30 | 0.0000 | 9.134e-006 | 7.2256e-005 | 389.2 |
| DIFF5 | 0.010 | 17.000 | 1.000 | 2000 | 0.30 | 0.0000 | 5.507e-006 | 1.5435e-004 | 343.0 |
| DIFF6 | 0.010 | 20.800 | 1.000 | 2000 | 0.30 | 0.0000 | 3.679e-006 | 2.8271e-004 | 310.1 |
| DIFF7 | 0.010 | 24.600 | 1.000 | 2000 | 0.30 | 0.0000 | 2.630e-006 | 4.6769e-004 | 285.1 |
| DIFF8 | 0.010 | 28.400 | 1.000 | 2000 | 0.30 | 0.0000 | 1.973e-006 | 7.1962e-004 | 265.4 |
| DIFF9 | 0.010 | 32.200 | 1.000 | 2000 | 0.30 | 0.0000 | 1.535e-006 | 1.0489e-003 | 249.2 |
| DIFF10 | 0.010 | 36.000 | 1.000 | 2000 | 0.30 | 0.0000 | 1.228e-006 | 1.4657e-003 | 235.7 |

Fig.18

| Element | Length (m) | Internal diameter (mm) | Wall thickness H (mm) | Young's modulus (MPa) | Poisson number | Hydr. resistance (mmHg/ml*min) | Hydr. inductance (mmHg*s/(ml/min)) | Hydr. Capacitance (ml/min*s/mmHg) | Wave speed (m/sec) |
|---|---|---|---|---|---|---|---|---|---|
| BSS Tube | 2.000 | 3.200 | 0.800 | 1 | 0.30 | 0.0973 | 0.0311 | 0.5147 | 15.8 |
| IRR Tube | 2.000 | 4.000 | 0.800 | 1 | 0.30 | 0.0399 | 0.0199 | 1.0053 | 14.1 |
| IRR Handpiece | 0.100 | 1.000 | 0.300 | | | 0.5103 | | | |
| ASP Handpiece | 0.060 | 0.800 | 0.300 | | | 0.7475 | | | |
| EYE R | | | | | | 6.3789 | | | |
| EYE C | | | | | | | | 0.0500 | |
| ASP Tube | 2.000 | 1.800 | 1.000 | 3 | 0.30 | 0.8722 | 0.0982 | 0.0244 | 40.8 |
| ASP Line | 0.100 | 1.800 | 1.000 | 2000 | 0.30 | 0.0486 | 0.0049 | 0.0000 | 1054.1 |
| K=30 | | | | | | | | | |
| DIFF1 | 0.010 | 1.800 | 1.000 | 2000 | 0.30 | 0.0049 | 4.912e-004 | 1.8322e-007 | 1054.1 |
| DIFF2 | 0.010 | 7.600 | 1.000 | 2000 | 0.30 | 0.0000 | 2.755e-005 | 1.3791e-005 | 513.0 |
| DIFF3 | 0.010 | 13.400 | 1.000 | 2000 | 0.30 | 0.0000 | 8.884e-006 | 7.5590e-005 | 386.3 |
| DIFF4 | 0.010 | 19.200 | 1.000 | 2000 | 0.30 | 0.0000 | 4.317e-006 | 2.2236e-004 | 322.7 |
| DIFF5 | 0.010 | 25.000 | 1.000 | 2000 | 0.30 | 0.0000 | 2.546e-006 | 4.9087e-004 | 282.8 |
| DIFF6 | 0.010 | 30.800 | 1.000 | 2000 | 0.30 | 0.0000 | 1.678e-006 | 9.1791e-004 | 254.8 |
| DIFF7 | 0.010 | 36.600 | 1.000 | 2000 | 0.30 | 0.0000 | 1.188e-006 | 1.5403e-003 | 233.8 |
| DIFF8 | 0.010 | 42.400 | 1.000 | 2000 | 0.30 | 0.0000 | 8.853e-007 | 2.3947e-003 | 217.2 |
| DIFF9 | 0.010 | 48.200 | 1.000 | 2000 | 0.30 | 0.0000 | 6.851e-007 | 3.5180e-003 | 203.7 |
| DIFF10 | 0.010 | 54.000 | 1.000 | 2000 | 0.30 | 0.0000 | 5.458e-007 | 4.9469e-003 | 192.5 |

Fig.19

DEVICE FOR REDUCING PRESSURE VARIATIONS IN AN ASPIRATION BRANCH, AND SURGICAL SYSTEM

CROSS-REFERENCE TO RELATED APPLICATIONS

This application is the National Stage of International Application No. PCT/EP2008/057717, filed Jun. 18, 2008, which claims the benefit of German Application No. 10 2007 031 722.2, filed Jul. 6, 2007. International Application No. PCT/EP2008/057717 is incorporated by reference herein in its entirety.

TECHNICAL FIELD

The invention relates to a device for reducing pressure variations of a fluid flowing in an aspiration branch of a surgical system, and to a surgical system, in particular an ophthalmic microsurgical system for lens surgery.

PRIOR ART

Phacoemulsification is a very frequently used technique in ophthalmology in which a surgical handpiece is used as a microsurgical tool. This handpiece generally comprises a tip in the form of a hollow needle with a relatively small diameter which can be designed for emulsifying, fragmenting and/or cutting tissue after said tip has been inserted into an incision in the cornea or sclera of the eye. Additionally, this tip of the handpiece can have a central channel which is connected to a suction source, for example a pump, which suctions off the tissue remains of the fragmented lens from the eye. Furthermore, the handpiece can be designed for supplying a rinsing fluid, for example a saline solution (BSS solution), to the eye for the purposes of rinsing the eye during the treatment. The removed tissue which is suctioned off from the eye together with the rinsing fluid is for example collected in a collection container which is usually arranged at a distance from the handpiece. The handpiece typically comprises an ultrasound apparatus for fragmenting the lens of the eye, which ultrasound apparatus excites the tip of the eye to oscillate. This oscillation of the tip fragments the lens into small parts.

The fluidics system in a phacoemulsification system is subdivided into two functional groups. The irrigation system waters the eye using a rinsing fluid during the operation. At the same time, a pump aspiration system suctions off the lens material that was emulsified as a result of the ultrasound process. These two functions of the fluidics module are connected to the phaco-handpiece by means of a flexible tube system. During the phase of operation, the rinsing fluid supply is controlled in the irrigation branch by an irrigation valve. The suction pressure is measured in the aspiration branch during the suctioning off and is used for monitoring and controlling the fluidics and ultrasound systems.

In said surgical systems, the pressure in the fluid can vary during operation of the components. This can occur in particular in the aspiration branch, as a result of which the suctioning off can only be effected in a suboptimal fashion and the surgical procedure can be adversely affected.

DESCRIPTION OF THE INVENTION

It is the object of the present invention to develop a device and a surgical system by means of which the frequency spectrum or the wavelength/amplitude spectrum of these pressure pulsations can be damped.

This object is achieved by a device and a surgical system according to the independent claims.

A device according to the invention is designed to reduce pressure variations in a fluid flowing in an aspiration branch of a surgical system. The device comprises a pump associated with the aspiration branch and, in particular, connected to the latter, and which pump is designed for delivering the flowing fluid in a discontinuous fashion in an active operational state. Pressure variations in the fluid are generated in the aspiration branch as a result of this pump and the method of operation thereof. Furthermore, the device comprises a diffuser arrangement which is arranged in the aspiration branch, upstream of the pump in the flow direction of the fluid. This device can change the frequency spectrum or the wavelength/amplitude spectrum of these pressure pulsations such that the damping effect is also significantly improved in the aspiration branch.

In the following context, the phrase damping of pressure variations is used instead of the term reduction of pressure variations, wherein a reduction should always be understood in terms of a detuning of a transmission characteristic of the system and not as energy destruction by energy conversion in the sense of classical damping.

A suction pump with a closed design is preferably used in the aspiration branch or on the aspiration side of a surgical system. This means that the pump has a design in which the fluid delivering or onward transporting elements of the pump do not come into direct contact with the fluid. In particular, a peristaltic pump can be used as a pump. However, pumps of the scroll pump or diaphragm pump design can likewise be utilized as well. It is precisely these types of pumps which, as a result of their design principles, are characterized in that they cannot generate a continuous fluid flow in an active operational state since the opening and closing valves or the roller wheels in each case remove a closed volume chamber from the suction region. This is the reason why these pumps also induce pressure pulsations in the flowing fluid in the aspiration branch of the operation equipment as a result of their flow pulses.

Since it is precisely such pumps, whose delivery elements are not in direct contact with the flowing fluid, which are preferably used in a surgical setting, not least for reasons of hygiene, such refinements in particular require a damping of the accompanying pressure variations during the discontinuous delivery of the fluid by the pump. This is required not least so as to not negatively influence the result of the operation.

The diffuser arrangement preferably comprises at least one diffuser. In principle, the designation "diffuser" is also understood to mean all of those elements which reduce the speed of wave propagation in such pressure variations in the flowing fluid, in particular those which can significantly reduce said speed. However, the amplitude of the pressure wave in particular should be reduced by the diffuser.

Provision is preferably made for the diffuser arrangement to comprise at least two diffusers. These diffusers can be designed as separate elements. In particular, provision can be made for the diffusers to be arranged at a distance from one another in the aspiration branch in the case of a number of diffusers. However, provision can likewise be made for the diffusers to be arranged directly adjacent to one another. Depending on the situation, an optimized number and an optimized arrangement of said diffusers to one another can be formed.

In the case of a multiplicity of diffusers, provision can be made for these to have the same design. These can in particular have the same design in respect of the shape and the dimensions and the selection of materials.

However, provision can likewise be made for at least two diffusers to have different designs. In particular, in this case too, there can be a difference in at least one of the following parameters: material selection, shape and dimensions.

If the diffuser arrangement comprises at least two diffusers, provision can be made for these to be connected or arranged in parallel. However, provision can likewise be made for at least two diffusers to be connected in series with one another as well. As a result of the series connection or the parallel connection of the diffusers, optimum damping of pressure variations according to the specific situation can also be achieved in this case because the frequency spectrum of the pressure pulsations in the flowing fluid or of the wave propagation can differ, depending on the other system parameters in the aspiration branch and further components of the surgical system. Individually, the arrangement of the diffusers can then damp specific frequency ranges in a very exact and precise fashion.

In the case of a multiplicity of diffusers, they can be detachably connected to one another. A virtually arbitrary number of diffusers can then be connected in a simple fashion and with little effort in order to be able to obtain a specific diffuser arrangement. This affords the possibility of a modular design of the diffuser arrangement.

Moreover, an individual diffuser can be replaced or serviced with little effort. Such a connection which can be detached without destruction and can be produced reversibly can also make cleaning work or the like simpler.

However, provision can likewise also be made for at least two diffusers to be connected to one another such that they cannot be detached. Such an integral design of the diffusers permits a cost-effective and simple production of the elements. Likewise, tolerances at the interfaces of the individual diffusers in the overall arrangement can thus be minimized in the case of a relatively complicated refinement. This can also have a positive influence on the mechanical stability.

The diffuser arrangement is preferably arranged in an aspiration line or an aspiration tube of the aspiration branch. This also affords the possibility of better utilization of the damping effect of an aspiration line or of the aspiration tube, which line or tube preferably can be at least in part elastically deformable as a result of the pressure variations in the flowing fluid.

The diffuser arrangement is preferably arranged between the pump and a surgical handpiece, at a distance from the pump arranged in the aspiration branch, and at a distance from said handpiece, in particular a phaco-handpiece, connected by an elastic aspiration tube of the aspiration branch. In this embodiment, the aspiration tube preferably constitutes the connection between the handpiece and the diffuser arrangement.

Provision can be made for the diffuser arrangement to be arranged in the aspiration branch such that it can be detached without destruction. Hence, this can also afford the possibility of simple reversible interchanging and reinserting or replacing of the diffuser arrangement in the case of a defect or for the purposes of cleaning.

However, provision can also be made for the diffuser arrangement to be designed in an integral and hence non-detachable fashion in the aspiration branch. This refinement can as it were provide an integral element which as a whole can quickly be inserted into or removed from the system. Moreover, such an integral design can also avoid critical points, for example in respect of tightness or the like. Moreover, the production can also be implemented in a cost-effective manner. By way of example, an injection-molded part can be provided in this respect.

A minimum internal dimension, in particular a minimum internal diameter, of the region of a diffuser, in particular the flow channel arrangement of the diffuser, through which fluid flows is preferably greater than or equal to a minimum internal dimension, in particular an internal diameter, of a front opening of a hollow needle of the handpiece. This dimensioning can prevent the remains of the lens suctioned into the hollow needle from catching in the diffuser arrangement and leading to a blockage.

The minimum internal dimension, in particular the internal diameter, of the diffuser arrangement preferably lies between 0.8 mm and 2.5 mm, in particular between 0.8 mm and 1.5 mm.

A maximum internal dimension, in particular an internal diameter, of the region of the diffuser arrangement through which fluid flows, and hence of the flow channel of the diffuser arrangement in particular, preferably lies between 1.2 mm and 25 mm, in particular between 1.5 mm and 15 mm. As a result of these dimensions of the minimum and maximum internal dimensions, it is possible to obtain an optimal damping of the pressure pulsations in the flowing fluid.

The length of the diffuser arrangement can depend on specific parameters of the fluid and/or the components associated with the aspiration branch. In particular, the length of the diffuser arrangement depends on the design of the lines and/or tubes of the aspiration branch and/or the pump and/or the diffuser arrangement itself. By way of example, the shape, the dimensions, the material and the attachment location, as well as the number of diffusers can be taken into account in this case.

The diffuser arrangement is preferably connected to an elastic aspiration tube in the aspiration branch and the length of the diffuser arrangement is preferably less than 15% of the length of the tube. The length of the diffuser arrangement is preferably less than or equal to 5%, in particular less than or equal to 2%, of the length of the tube. The shorter the length of the diffuser arrangement compared to the other components, the easier and more flexible the handling and applicability of the arrangement. In particular, a compact and installation-space minimized design can also be obtained as a result of this. Not least, this can also save weight and this leads to significantly improved usability and easy applicability, particularly when the diffuser arrangement is attached in the vicinity of the handpiece which has to be held and moved by the operator.

The diffuser arrangement preferably has a length of between 10 mm and 400 mm, in particular between 90 mm and 300 mm, preferably less than or equal to 200 mm. These ranges of the length permit a particularly suitable design in respect of installation-space minimization and effective damping of the pressure pulsations. However, the length of the diffuser arrangement can also lie between 100 mm and 400 mm or between 20 mm and 200 mm. Depending on the system, the respectively optimum geometry can then be selected.

By way of example, the wave frequency of the pressure pulsation in the flowing fluid and/or the density of the fluid and/or the wall thickness of the diffuser arrangement or of a diffuser and/or Young's modulus E of the wall of the diffuser can be taken into account as a specific parameter or specific parameters, as a function of which the length and geometry of the diffuser arrangement is advantageously formed. The wave propagation can be determined in a three-dimensional simulation on the basis of these parameters and additional variables such as, for example, the local diameter of the diffuser and/or the dynamic viscosity of water, and a suitable geometry of the diffuser arrangement can then be determined there-from. In the process, a ratio K between a maximum and a minimum internal dimension of the diffuser arrangement is preferably determined and changed as a variable in the simulation for the purposes of optimization. In particular, the variable K is the main influencing factor in respect of damping the pressure wave in the fluid.

Provision can be made for an inner side of the diffuser arrangement, which constitutes a boundary of the region of the diffuser arrangement through which fluid flows and hence in particular defines a wall of a flow channel, to be at least in part elastic to forces acting as a result of pressure pulses or pressure waves in the fluid. However, provision can likewise also be made for such an inner side of the diffuser arrangement to be at least in part stiff to forces acting as a result of the fluid and hence be non-deformable.

The diffuser arrangement is preferably arranged in a fluidics cassette of the device. This can ensure protection against damage and afford the possibility of a mechanically stable attachment. Simple replacement of the entire cassette from the device is thereby ensured, and simple access to the diffuser arrangement is made possible. Thus, as it were, the diffuser arrangement is thereby furthermore arranged in a larger housing, as a result of which there is little wear and tear, even in the case of multiple removal and reinsertion of the cassette into the system.

If the diffuser arrangement comprises a multiplicity of diffusers, provision can be made for at least one diffuser to be arranged in the cassette.

At least one diffuser in the diffuser arrangement preferably has a continuously increasing internal dimension over its length, starting from a minimum internal dimension and up to a maximum internal dimension.

One inner side of a diffuser in the diffuser arrangement preferably has at least in part a curved design in the longitudinal direction of the diffuser. Provision can also be made for an inner side of a diffuser in the diffuser arrangement to have at least in part a stepped design in the longitudinal direction of the diffuser.

The diffuser arrangement preferably has a ratio K between its maximum internal dimension and its minimum internal dimension, wherein the minimum and the maximum internal dimensions are preferably formed at the end openings of the diffuser arrangement.

The diffuser arrangement preferably has a ratio K between its maximum internal dimension and its minimum internal dimension which is greater than or equal to 2. Particularly in the case of a round cross section, the internal dimension is shaped as an internal diameter. The diffuser arrangement preferably has a ratio K between its maximum internal dimension and its minimum internal dimension which is greater than or equal to 5, in particular greater than or equal to 10. Relatively small values of K can already achieve significant damping, particularly of the amplitude of the generated pressure wave. In addition to the more important damping of the amplitude of the wave, the phase speed or wave propagation speed c is also varied thereby.

In completely general terms, in the present context, as mentioned above, a damping or reduction is understood to be less of a damping in the classical sense but, in particular, it should be understood to be the change of the transmission characteristics of the device for the wave. The device therefore damps in the sense of a detuning of the transmission properties of the components, which is also referred to as an impedance transformation. The diffuser arrangement effects a shift in the resonances and the diffuser arrangement prevents the excitation of a standing wave in the relevant frequency range within the aspiration system comprising the suction line, the aspiration tube, the handpiece, the aspiration line, the diffuser arrangement and the pump. The larger the ratio K, the more efficiently this can be achieved.

A surgical system according to the invention, in particular an ophthalmic microsurgical system, for lens surgery comprises a pump delivering in a discontinuous fashion in an active operational state which is associated with an aspiration branch of the system and which is preferably connected to an aspiration line of the aspiration branch. Moreover, the surgical system comprises a surgical handpiece connected to the aspiration branch. Furthermore, the surgical system has a device for reducing pressure variations of a fluid flowing in the aspiration branch of the surgical system, the pressure variations being generated during the operational state of the pump, which device comprises a diffuser arrangement arranged in the aspiration branch, upstream of the pump in the flow direction of the fluid. This can prevent an impairment of an operation as a result of pressure variations in the fluid, particularly in cataract operations in which a lens is removed from the eye by means of phacoemulsification.

Advantageous embodiments of the device according to the invention for damping pressure variations should be considered to be advantageous embodiments of the surgical system.

BRIEF DESCRIPTION OF THE DRAWINGS

Exemplary embodiments of the invention are explained in more detail below on the basis of schematic drawings, in which

FIGS. 5a to 5k shows cross-sectional illustrations of different shapes of a diffuser arrangement;

FIG. 6 shows a model of a surgical system known from the prior art;

FIG. 7 shows a flow-technical replacement circuit diagram for a component of the model in accordance with FIG. 6;

FIG. 8 shows an exemplary embodiment of a model of a surgical system according to the invention;

FIG. 9 shows a flow-technical replacement circuit diagram for a component of the model in accordance with FIG. 8;

FIG. 16 shows a first table which shows parameter values for a simulation of the model illustrated in FIG. 6;

FIG. 17 shows a second table which shows values of parameters and variables for a simulation of a model illustrated in FIG. 8 for a first exemplary embodiment of a surgical system according to the invention;

FIG. 18 shows a third table which shows values of parameters and variables for a simulation of a model illustrated in FIG. 8 for a second exemplary embodiment of a surgical system according to the invention;

FIG. 19 shows a fourth table which shows values of parameters and variables for a simulation of a model illustrated in FIG. 8 for a third exemplary embodiment of a surgical system according to the invention.

PREFERRED EMBODIMENT OF THE INVENTION

In the figures, the same or functionally equivalent elements are provided with the same reference signs.

Figure 1:
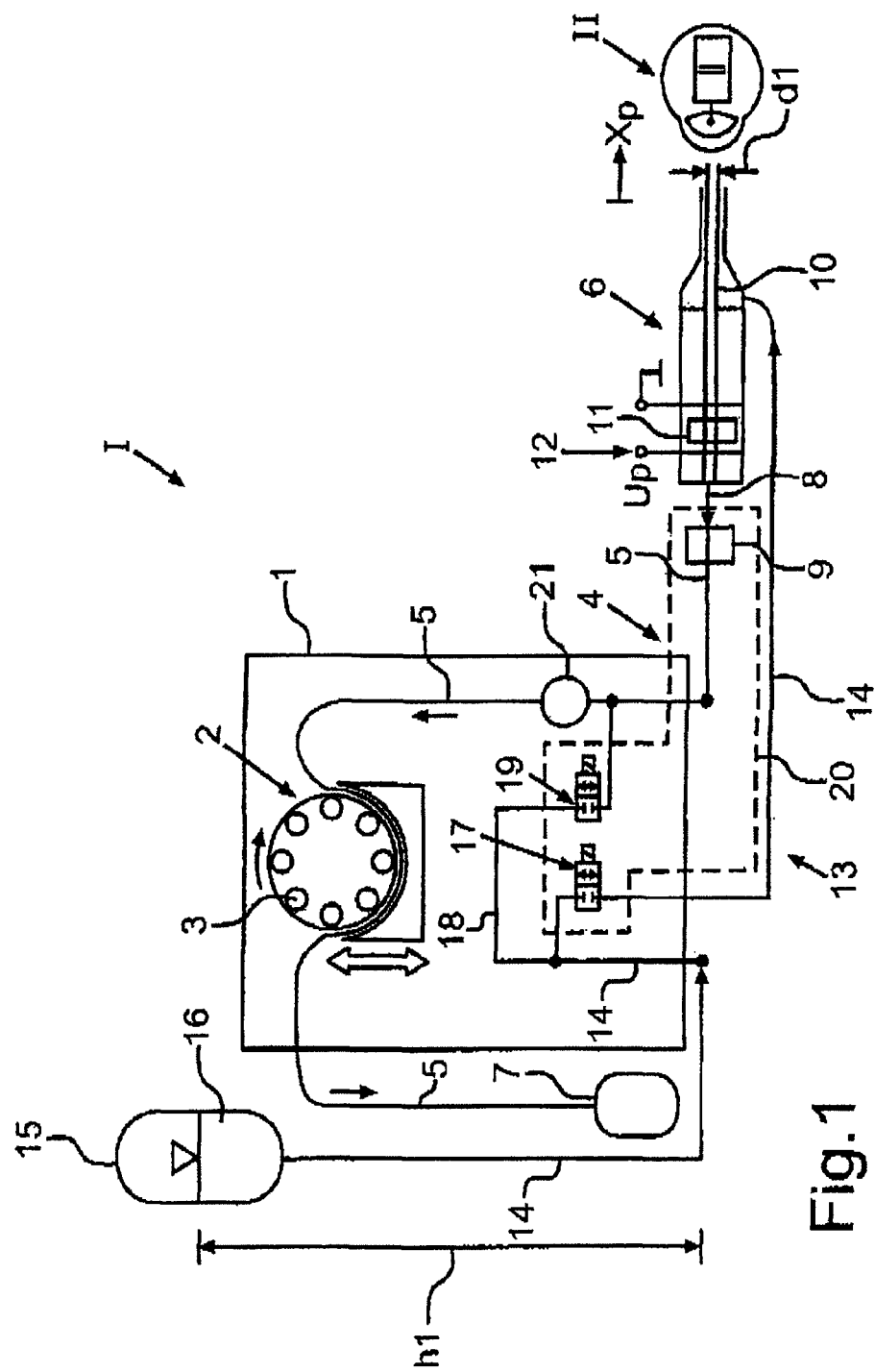
FIG. 1 shows a schematic illustration of parts of a surgical system according to the invention.

FIG. 1 shows, in a schematic illustration, an ophthalmic microsurgical system I for lens surgery. Only the essential components of the system I which are required for understanding the invention are shown in the illustration in accordance with FIG. 1.

The surgical system I comprises an equipment unit 1 which can, for example, be designed as a trolley or the like and which also has a pump 2 in addition to electrical control units, electronic driver units for microsurgical instruments, a user interface and a display unit. In the exemplary embodiment, this pump 2 is designed as a peristaltic pump and hence as a pump which delivers in a discontinuous fashion in an active operational state. The pump 2 comprises a multiplicity of roller wheels 3 which are arranged at a distance from one another in the direction of the rotation (arrow) and which each remove a closed-off volume chamber from the suction region.

The pump 2 is arranged in an aspiration branch 4 of the surgical system I and delivers the liquid which flows in an aspiration line 5 of the aspiration branch 4, from a surgical handpiece 6, which is the phaco-handpiece in the exemplary embodiment, to a collection container 7. In the illustrated embodiment, the aspiration branch 4 also comprises an elastic aspiration tube 8 (ASP tube) which extends between the handpiece 6 and a diffuser arrangement 9 arranged in the aspiration branch 4. The diffuser arrangement 9 is preferably arranged as close as possible to the pump 2.

As a result of its design, the pump 2 is conceived such that the roller wheels 3 are designed so as not to contact the fluid flowing in the aspiration line 5 and so there is no direct connection between the roller wheels 3 and the fluid.

The handpiece 6 comprises a tip or a hollow needle 10 which is excited to oscillate by an ultrasound transducer 11. By way of example, the ultrasound transducer 11 can be piezoelectric and be excited to oscillate by an electrical voltage. The voltage is generated by a symbolically illustrated voltage source 12. An opening with a diameter d1 is provided on the front side of the hollow needle 10, which faces the eye II. The diameter d1 is smaller than the diameter of the remainder of the hollow needle 10, as a result of which the hollow needle 10 has a tapered design at this front opening.

Moreover, the surgical system I comprises an irrigation branch 13 with an irrigation line 14 which extends between a container 15 with a rinsing fluid 16 and the handpiece 6. By way of example, the rinsing fluid 16 can be a saline (BSS solution). The illustration in FIG. 1 shows that the container 15 is at a height-level h1 compared to the handpiece 6, as a result of which the pressure of the rinsing fluid 16 in the irrigation line 14 can be varied as a function of this height h1. Furthermore, a valve 17 is arranged in the irrigation line 14. The irrigation line 14 is connected to the aspiration line 5 by a tube connection 18, with a further valve 19 being arranged in this tube connection 18.

The irrigation line 14 is preferably designed at least in part as an elastic tube (IRR tube) extending between the handpiece 6 and a fluidics cassette 20. The cassette 20 can at least partly comprise the diffuser arrangement 9. Provision can likewise be made for the cassette 20 to comprise the valves 17 and 19. The irrigation line 14 can also be designed as an elastic tube (BSS tube) between the container 15 and the cassette 20. The part of the aspiration line 5 located in the cassette 20 will also be referred to as an ASP line in the following text.

Moreover, a pressure gauge 21 is arranged in the aspiration branch 4, which gauge is connected, in the aspiration line 5 in the exemplary embodiment, downstream of the connection line 18 to the irrigation line 14 in the flow direction of the fluid.

During the surgical procedure on the eye II, the rinsing liquid 16 supplied via the irrigation line 14 is suctioned off with the fragmented remains of the lens by the pump 2 via the hollow needle 10 and the aspiration branch 4.

The surgical system I furthermore comprises a device for reducing or damping pressure variations of the fluid flowing in the aspiration branch 4, the pressure variations being generated by the pump 2 delivering in a discontinuous fashion. This device for damping the pressure variations comprises the diffuser arrangement which is arranged in the aspiration branch 4, upstream of the pump 2 in the flow direction (arrow) of the fluid.

In FIG. 1, the diffuser arrangement 9 is merely illustrated by a symbolic block element and is arranged relatively close to the handpiece 6. In the illustrated embodiment, the diffuser arrangement 9 is arranged at a distance from both the handpiece 6 and the pump 2. Provision can also be made for the diffuser arrangement 9 to at least in part be arranged in the handpiece 6 or to be arranged directly on the back end of the handpiece 6 which opens into the aspiration tube 8.

The device for damping these pressure variations using the diffuser arrangement 9 can, in the aspiration branch 4, damp the frequency spectrum or the wavelength/amplitude spectrum of these pressure pulsations in the flowing liquid. In particular, this arrangement can also improve the damping effect of the elastic aspiration tube 8.

Figure 2:
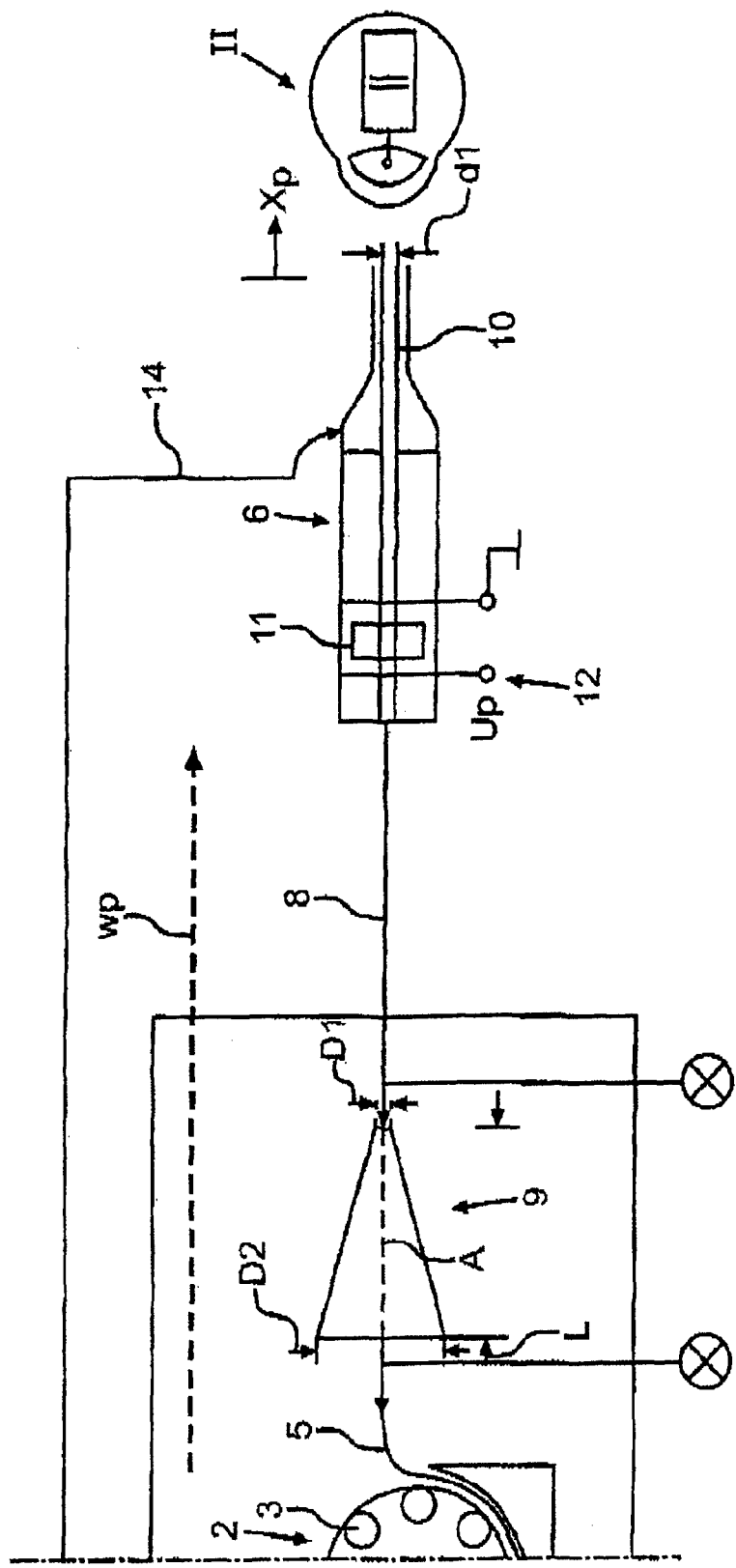
FIG. 2 shows a schematic illustration of a partial section of the surgical system in accordance with FIG. 1.

FIG. 2 shows a schematic illustration of a partial section of the surgical system I in accordance with FIG. 1. In this exemplary embodiment, the diffuser arrangement 9 merely comprises one diffuser of a funnel-shaped design which opens up in the aspiration branch 4 in the flow direction of the fluid. The diffuser has a minimum internal dimension D1 on its side facing the handpiece 6. In particular, provision can be made for the diffuser to have a substantially round cross section and so the internal dimension is the internal diameter. This minimum internal dimension D1 is equal to or greater than the minimum internal dimension, in particular the internal diameter, d1 of the hollow needle 10. In particular, the minimum internal dimension D1 of the diffuser arrangement 9 is between 1 mm and 2 mm.

The diffuser has a maximum internal dimension D2, in particular an internal diameter, on the end side of the diffuser arrangement 9 facing the pump 2, and, in the exemplary embodiment, this dimension at the same time constitutes the maximum internal dimension of the diffuser over its length L.

In the illustrated embodiment, the internal dimensions D1 and D2 are defined at the end openings of the diffuser arrangement 9 or of the only diffuser.

In particular, the maximum internal dimension D2 lies between 1.5 mm and 10 mm.

Additionally, the diffuser arrangement 9 and hence (in the illustrated embodiment) the only diffuser has a length L which can be prescribed depending on specific parameters of the fluid and/or of components associated with the aspiration branch 4, for example the aspiration tube 8, and/or the pump 2 and/or the diffuser arrangement 9 itself. The shape, the dimensions, the material and the arrangement of the components with respect to one another in particular can in this respect influence the length L. However, in order to be able to obtain optimum damping of the pressure variations, the ratio K between the maximum and the minimum internal dimension D2 and D1 in particular has to be dimensioned in an optimum fashion.

This determination of the variable K and the shape of the diffuser arrangement 9 can preferably be obtained by a simulation calculation.

In the embodiment of the only diffuser in the diffuser arrangement 9 illustrated in FIG. 2, said diffuser has a symmetric design with respect to the rotational axis A.

FIGS. 3a to 3i illustrate further exemplary embodiments of a diffuser arrangement 9; it goes without saying that the invention also comprises refinements of a diffuser arrangement 9 which go beyond said embodiments and are not illustrated.

Figure 3A:
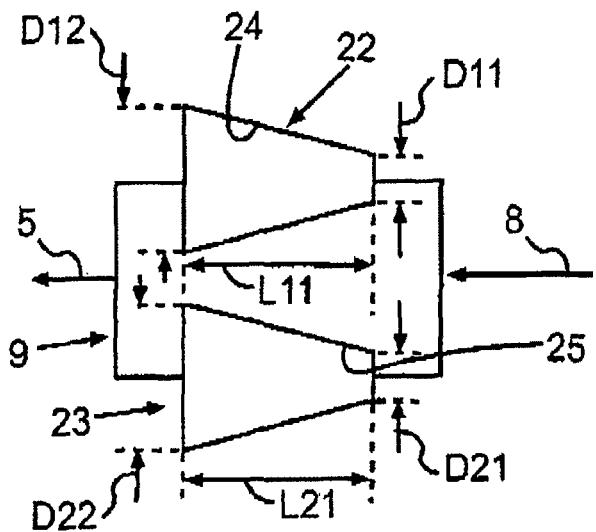
FIGS. 3a to 3i show embodiments of a diffuser arrangement of a device according to the invention.

FIG. 3a schematically illustrates a further exemplary embodiment of a diffuser arrangement 9. In this embodiment, the diffuser arrangement 9 comprises at least two diffusers 22 and 23, connected in parallel. In the illustrated embodiment, both diffusers 22 and 23 have the same design and thus have the same shape and same dimensions and are made of the same material. The two diffusers 22 and 23 are each oriented such that their ends facing the handpiece 6 each have the minimum internal diameter. The first diffuser 22 has a minimum internal dimension D11 and the second diffuser 23 has a minimum internal dimension D21. Both diffusers 22 and are arranged and designed such that their ends facing the pump 2 each have the maximum internal dimension. Thus, the first diffuser 22 has a maximum internal dimension D12 and the second diffuser 23 has a maximum internal dimension D22. Moreover, the first diffuser 22 has a length L11 which corresponds to the length L21 of the second diffuser 23. Both diffusers 22 and 23 are designed such that they continuously widen, starting from their respective ends facing the handpiece 6 with the minimum internal dimension D11 and D21, up to their respective other ends with the maximum internal dimensions D12 and D22. Furthermore, the inner sides 24 and 25 have a straight-lined design over the entire length between the two ends of the diffusers 22 and 23 and hence have a design without curves. This results in both diffusers 22 and 23 being shaped like a frustum.

Provision can also be made for the diffusers 22 and 23 to have different shapes and/or dimensions and/or to be made of different materials. Provision can likewise also be made for the first diffuser 22, for example, to be arranged connected in parallel and in an arrangement rotated by 180°. This is illustrated in FIG. 3d in an exemplary and symbolic fashion. In this embodiment, the end with the maximum internal dimension D12 would face the handpiece 6.

Figure 3B:
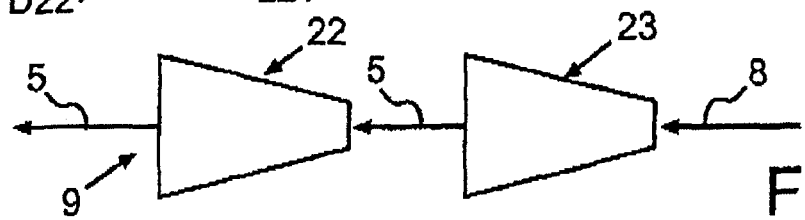

FIG. 3b shows a further embodiment of a diffuser arrangement 9 in which at least two diffusers 22 and 23 are connected in series with one another. In the exemplary embodiment, the two diffusers 22 and 23 have a design that is analogous to the diffusers 22 and 23 from FIG. 3a. In FIG. 3b, the diffusers 22 and 23 are arranged in the aspiration branch 4, at a distance from one another.

Provision can also be made for the diffusers 22 and 23 to be arranged directly adjacent to one another. In this case too, it is again possible for the diffusers 22 and 23 to be different in terms of shape and/or dimensions and the like.

Figure 3C:
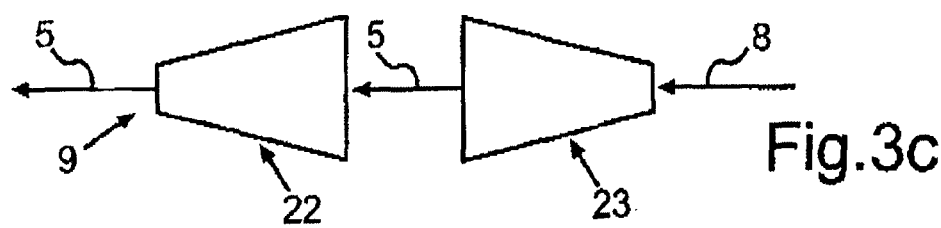
Figure 3D:
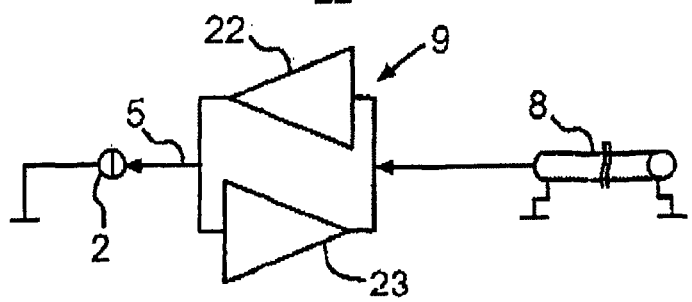
Figure 3E:
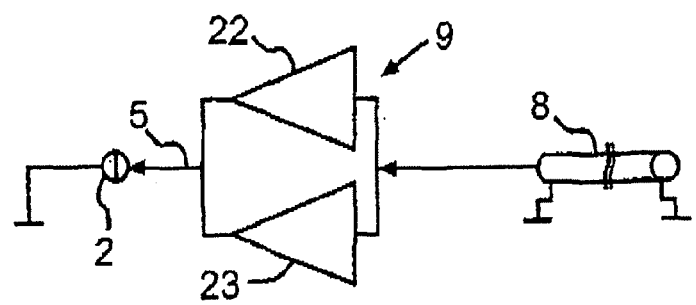
Figure 3F:
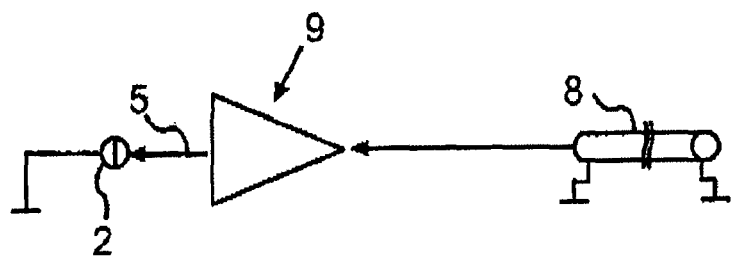
Figure 3G:
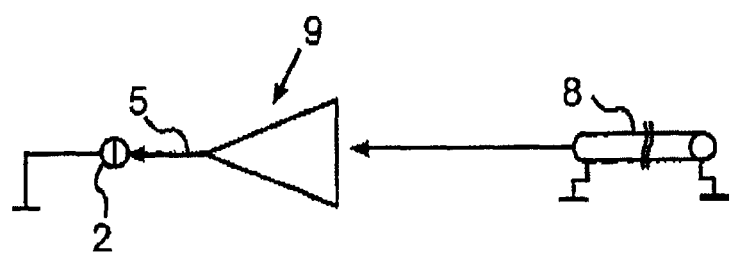
Figure 3H:
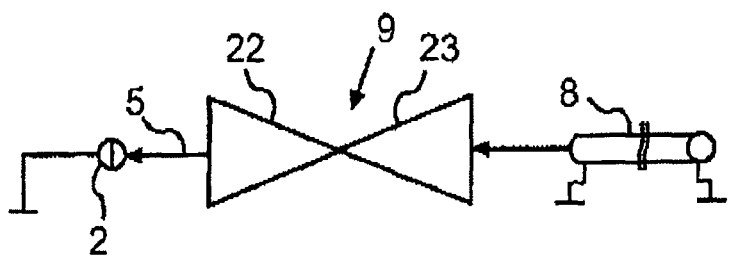
Figure 3I:
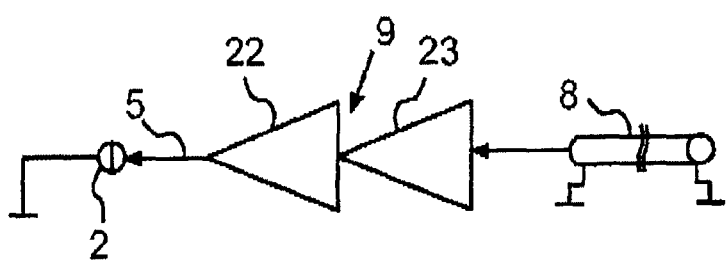

FIG. 3c shows a further embodiment of a series connection of diffusers 22 and 23 in a diffuser arrangement 9, in which the ends of the diffusers 22 and 23 with the maximum internal dimensions face one another. Hence, the diffuser arrangement 9 overall has a design which first of all has a very small internal dimension, which then expands to a maximum internal dimension and which, starting from this maximum internal dimension, then again tapers off to a small, in particular minimum, internal dimension. In this embodiment according to FIG. 3c, provision can also be made for the two diffusers 22 and 23 not to be at a distance from one another but rather be directly adjacent to one another.

The inner walls 24 and 25 of the diffusers 22 and 23 can be at least in part elastic to actions of force which can be generated as a result of pressure pulsations in the fluid which flows through said diffusers.

Provision can likewise be made for the inner sides 24 and 25 to be completely stiff and hence non-deformable by such actions of force.

FIGS. 3e to 3i show further exemplary embodiments of a diffuser arrangement 9, illustrated by corresponding symbols. Here, further embodiments of parallel connections and series connections of at least two diffusers in a diffuser arrangement 9 are shown. In principle, the number of diffusers is not restricted to one or two, but provision can also be made for a larger number.

FIGS. 4a to 4f show embodiments of longitudinal sectional illustrations of a diffuser arrangement 9.

Figures 4A, 4B:
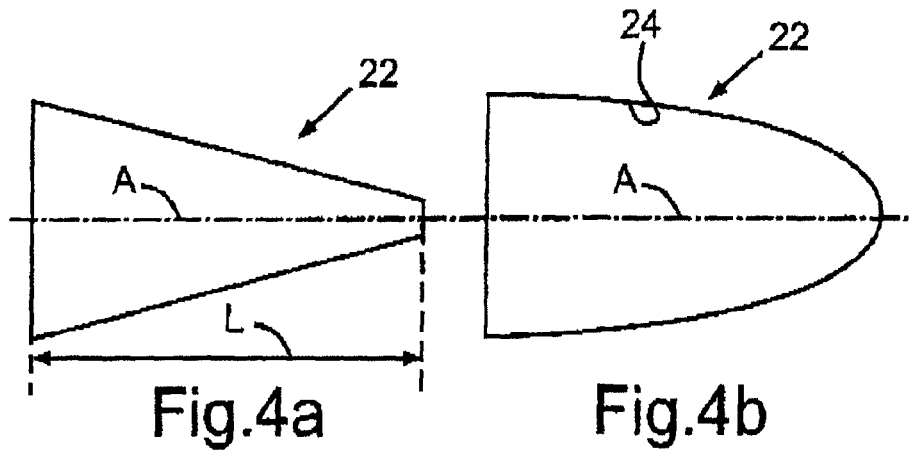
FIGS. 4a to 4f show longitudinal sectional illustrations of different shapes of a diffuser arrangement.

FIG. 4a shows a sectional illustration through a diffuser arrangement 9 which has a diffuser 22 with a strict frustum-shaped shape. This means that the inner side 24 constitutes as it were a straight line over the length L of the illustrated sectional illustration, which straight line runs obliquely between the ends of the diffuser 22.

FIG. 4b shows a further exemplary shape of a diffuser in a longitudinal sectional illustration. In this embodiment, the inner side or the shell of the inner sides 24 has a curved profile when viewed in the direction of the axis A. The curvature in this case has a profile which as it were arches outward.

Figures 4C, 4D:
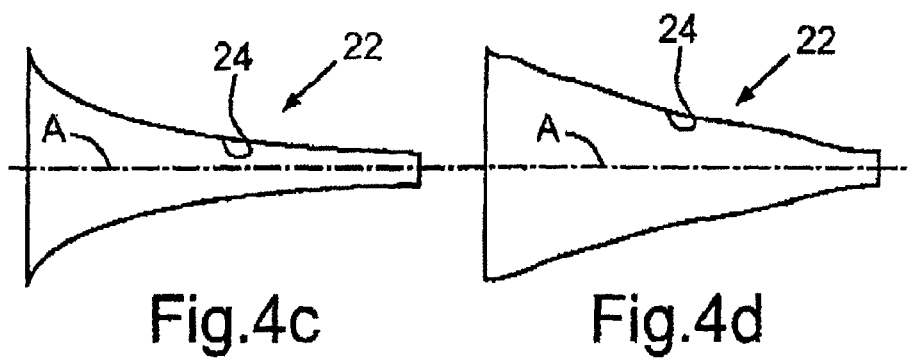

FIG. 4c shows a further sectional illustration of an exemplary embodiment of a diffuser 22 which likewise has an inner side 24 with a curved profile. Like in the embodiment in accordance with FIG. 4b, the curve is here also formed over the entire length L; however, in the embodiment in accordance with FIG. 4c, the curvature is not arched outwardly but it is arched inwardly.

A further embodiment of a shape of the inner side 24 of a diffuser 22 is shown in the longitudinal sectional illustration in accordance with FIG. 4d. In this embodiment, the inner side 24 has a multiply waved profile over the length L, as a result of which, as it were, a free-form contour is created. Hence, the inner side 24 has a wave-shaped design in the sectional illustration.

Figure 4E:
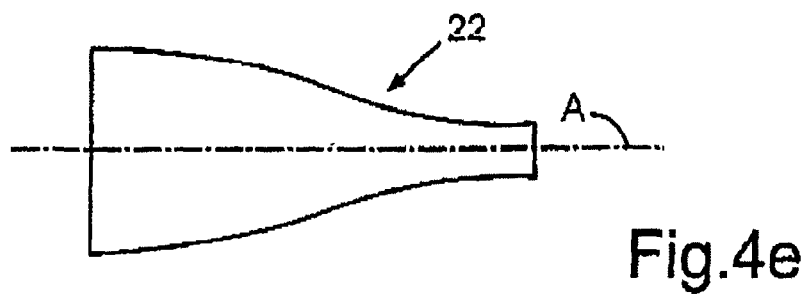

FIG. 4e shows a further shape in which an embodiment which is symmetric with respect to the axis A is formed and is strongly tapered in approximately the center.

Figure 4F:
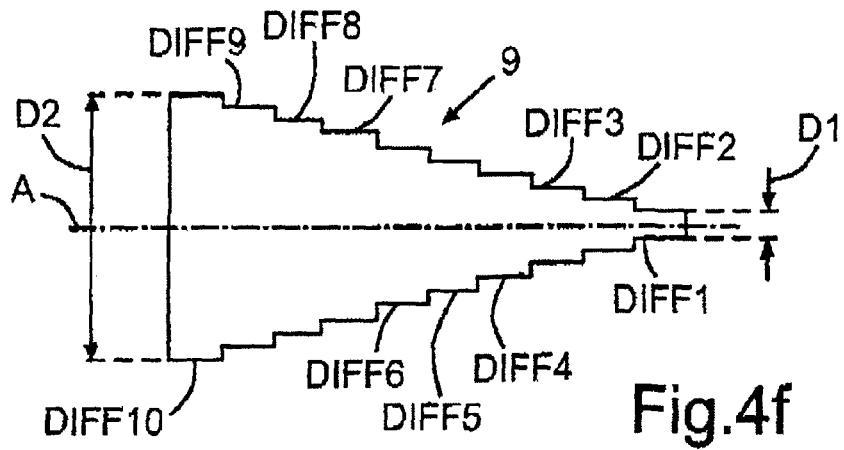

FIG. 4f illustrates a stepped shape which comprises ten different partial segments DIFF1 to DIFF10. Such a refinement is also suitable as an auxiliary construction in respect of a model calculation by a simulation. The number of partial segments is merely exemplary and can be designed differently in a number of ways. Particularly in the case of a very complicated contour profile, a very large number of partial segments can also be provided which then have minimal partial lengths in the direction of the axis A and hence in the longitudinal direction of the diffuser arrangement 9, wherein a step-free contour profile is then obtained and can be calculated by integration as a result of a relatively small change in the internal dimension between two successive partial segments. The sum of the partial lengths then results in the overall length L.

FIGS. 5a to 5k show cross-sectional illustrations of different embodiments of a diffuser arrangement 9.

FIGS. 5a to 5k show schematic views which have been selected such that, in the direction of the longitudinal axis A, the view is from the end with the larger internal dimension toward the other end with the smaller internal dimension. Here, FIG. 5a shows a completely round shape of the two end regions with the internal diameters D2 and D1.

FIG. 5b shows an embodiment with angular, in particular square, end shapes.

FIG. 5c in turn shows a shape in which the end regions have four corners, but in this case they are rectangular.

FIG. 5d shows a corner-free refinement of the ends of the diffuser arrangement 9, but it has a flattened, in particular oval, design.

FIG. 5e shows a triangular shape of the ends.

FIG. 5f shows an embodiment in which the opposing ends of the diffuser arrangement 9 have different shapes, which respectively illustrate a free-from contour.

FIG. 5g shows a refinement which is nonsymmetrical in respect of a horizontal axis and which in each case shows semicircles at both ends of the diffuser arrangement 9. FIG. 5h illustrates a similar shape, with FIG. 5i once again showing free-form contours at both ends.

FIGS. 5j and 5k show further asymmetrical embodiments, with the internal dimensions D1 and D2 being internal diameters of the round cross sections in FIG. 5j, and the contours of the end openings of the diffuser arrangement 9 in FIG. 5k being partly curved but also having corners.

In general, what can be achieved by the invention is that the wave speed and in particular the amplitudes of pressure variations or pressure waves in the flowing fluid in the aspiration branch can be significantly reduced in the region of the diffuser arrangement of the device for damping these pressure variations.

The pump 2 designed as a peristaltic pump can for example have eight roller wheels 3. By way of example, it can have a rated speed of 600 rpm and a delivery rate of 60 ml/min. In the process, the rated range of the pulsation frequency for example extends from 0 to approximately 80 Hz.

Polycarbonate can preferably be used as a material for a diffuser arrangement 9 or a diffuser 22 or 23. This material selection affords the possibility of a cost-effective refinement which can be produced easily. In particular, the diffuser arrangement 9 can be produced as an injection-molded part. As a result of this material selection and production method, a multifaceted design and most complex shapes of a diffuser arrangement 9 are also made possible. Moreover, these materials afford the possibility of a very light diffuser arrangement 9. In addition to a polycarbonate, it is also possible to use a silicone material which can be designed as both a hard and a soft silicone material.

FIG. 6 shows a standard operation system with an operation handpiece in a model for a simulation. The fluidics system for this phacoemulsification system is subdivided into two functional groups. During the cataract operation, the irrigation system waters the eye with BSS solution. At the same time, a pump aspiration system suctions off the cataract material emulsified by the ultrasound process. With these two functions, the fluidics module is connected to the phaco-handpiece via a flexible tube system.

Starting point for the irrigation system is the replacement rinsing liquid BSS. As a result of the flask which can be positioned at a height, the BSS solution acts as a hydrostatically constant pressure source for the irrigation system. The BSS flask is connected to the fluidics of the equipment by a flexible elastic BBS tube 141.

The hydrostatic pressure can be determined by the following physical law:

$$p = \rho \cdot g \cdot h.$$

The density $\rho$, the acceleration due to gravity g and the flask height h (in the exemplary embodiment in accordance with FIG. 1 this is h1) each determine the hydrostatic pressure p in the irrigation system of the surgical system I as a linear influencing variable. In the case of the density $\rho$ of the BSS solution, all considerations assume a value of $\rho=1000$ kg/m$^3$. In all further considerations, a hydrostatic pressure of 50 mmHg is assumed as a result of the height of the BSS flask.

The suction flow Q in the fluidics system of the surgical system I is implemented by the pump 2. During the suctioning, the suction pressure p in the aspiration branch 4 is measured (sensor in the cassette 20) and used for monitoring and controlling the fluidics and ultrasound systems. The pump 2, as a result of its design principle, does not deliver a continuous flow Q(t) since the opening and closing valves or the roller wheels 3 in each case remove a closed-off volume increment from the aspiration region. Hence, the pump 2 induces pressure pulsations p(t) in the aspiration branch of the operation equipment as a result of its flow pulses Q(t).

These pressure pulsations p(t) propagate as longitudinal waves along the aspiration branch 4 in the direction of the eye II to be operated on. They are partly reflected in the region of the aspiration line of the handpiece 6. However, a certain proportion of these pulsation waves reach the chamber of the eye opened by the surgical incision via the aspiration line of the handpiece 6. The intraocular pressure is thereby likewise excited to pressure oscillations in the chamber of the eye. This is a very disadvantageous characteristic for the course of the operation. The operator notices the pressure oscillations as a pulsating eye. This disturbs the very delicate procedure greatly.

The invention finds a solution which can at least strongly reduce the pulsation excitation in the eye by the pressure waves in the aspiration branch 4.

According to the prior art, this could be effected by arranging a capacitor in the vicinity of the pump 2 exciting the pulsations or by increasing the elasticity of the aspiration line. However, this has to be avoided at all costs for methodological reasons because, in the case of an occlusion of the aspiration needle, the elastic aspiration line which has a very high vacuum pretension and the elastic aspiration tube could briefly suction off dangerously large amounts of liquid from the chamber of the eye when there is a break through the occlusion. This pressure wave, known by the term "surge", endangers the success of the eye operation and has to be avoided. Furthermore, the posterior capsular bag of the eye can sustain cut injuries as a result of these pulse-like suction forces at the tip of the hollow needle 10 of the handpiece 6. It is for this reason that the aspiration branch 4 has to be equipped with the lowest elasticity possible between the handpiece 6 and the pump 2.

Damping the pulsation by increasing the elasticity of the line and tubes in the aspiration branch or by arranging an additional capacitor can therefore be eliminated.

A further possibility for damping pressure waves according to the prior art would be to increase the hydraulic resistance by reducing the cross sections of the aspiration line. However, since an emulsion is intended to be transported away from the eye, all internal cross sections of lines and tubes in the aspiration branch 4 should be designed to be significantly larger than the narrowest cross section in the hollow needle 10 so that the aspiration line system cannot be blocked and the pressure loss as a result of the flow does not become too large. Therefore, this possibility can likewise be eliminated.

It is intended that a brief discussion follows as to how the occurring longitudinal pressure waves in the aspiration branch 4 and the pressure oscillations in the eye II excited thereby can be calculated and illustrated on the basis of a hydraulic simulation model.

In the case of laminar pipe flow, the hydraulic resistance $R_h$ in a line can be determined according to the Hagen-Poiseuille law as $$R_h = \frac{8 \cdot \eta \cdot l}{\pi \cdot r^4}.$$

Here, the internal radius r of the line goes as the inverse of the fourth power. The length l of the line and the dynamic viscosity $\eta$ of the liquid go linearly in this case. The unit of the hydraulic resistance can be expressed in, for example, [mmHg/ml*min].

The hydraulic line has an inductance $L_h$. The hydraulic inductance characterizes the dynamic change in pressure due to the inertia of the liquid volume to be accelerated. It can be determined according to the following formula:

$$L_h = \frac{\rho \cdot l}{A}.$$

Together with the line length l and the internal line cross section A, the density $\rho$ of the liquid determines the hydraulic inductance $L_h$, the unit of which can be expressed in [mmHg*s/(ml/min)].

As a first approximation, the elastic properties of the tube line are determined by the material properties of the wall material. In the case of a soft silicone tube, a Young's modulus $E_{soft}$=1 MPa is assumed; a hard PVC or silicone tube has a Young's modulus of $E_{hard}$=3 MPa. Hence, the hydraulic capacitance $C_h$ can be determined by the elastic properties $E_{wall}$ of the tube or wall material of the lines according to the following equation:

$$C_h = \frac{V_0 \cdot 2 \cdot r}{E_{wall} \cdot h}.$$

Here, $V_0$ refers to the liquid volume enclosed by the line. The wall thickness h of the line wall, as well as the internal radius r of the line and the Young's modulus $E_{wall}$ of the elastic wall determine the capacitive properties of the elastic line with the possible unit [ml/min*s/mmHg].

Using the hydraulic capacitance $C_h$ and the inductance $L_h$ of an elastic line as a starting point, the propagation speed c of the pressure waves can be determined according to the following formula:

$$c = \frac{1}{\sqrt{L_h \cdot C_h}} = \sqrt{\frac{E_{wall} \cdot h}{2 \cdot r \cdot \rho}}.$$

The unit of the wave propagation speed or phase speed c is [m/s]. It can be seen that the lengths cancel in the formula for the wave propagation speed c in accordance with the rear expression of the formula.

According to the abovementioned determination equations, in the case of an aspiration tube with an internal radius r=0.9 mm and a Young's modulus of $E_{wall}$=3 MPa for a hard PVC tube and a wall thickness h=1 mm, this leads to a wave propagation speed c=40.8 m/s. The Young's modulus of the elastic wall material determines this phase speed c of the pressure wave in a dominant fashion.

The propagation of a one-dimensional wave can be described by a 2nd order partial differential equation. It is called the wave equation or d'Alembert's equation.

$$\frac{\partial^2 p}{\partial t^2} = c^2 \frac{\partial^2 p}{\partial x^2}$$

The solution of the hyperbolic wave equation is found using numerical methods such as the method of characteristics.

In accordance with illustration 1, a fluidics simulation is performed by using, for example, the calculation software Matlab/Simulink from Mathworks.

FIG. 6 illustrates the hydraulic arrangement of the individual elements in a model according to the prior art. In addition to the already known reference signs, which have been described above, and their associated components, a part 26 of the aspiration line (ASP line) arranged in the cassette 20, a pressure gauge 27 for the irrigation branch 13, an element 28 characterizing a resistance in the handpiece 6 of the irrigation part in a flow-technical fashion, an element 29 characterizing the hollow needle 10 as a resistor in a flow-technical fashion and a further pressure gauge 30 are illustrated in an exemplary fashion.

Furthermore, in accordance with the model, FIG. 6 shows an element 31 (EYE C) characterizing the capacitance of the eye II in a flow-technical fashion and a flow resistance 32 (EYE R), as well as a switch 33 characterizing the breakthrough of a lens particle 6 in the handpiece 33. Moreover, an elastic irrigation tube 140 and a further elastic tube (BSS tube) between the container 15 and the cassette 20 are symbolized by the element 141 in an exemplary fashion.

The elastic lines relevant for the propagation of the pressure waves are illustrated by the line symbol. The calculation software Simulink discretizes the elastic line into a number of small segments which are each represented by an individual elasticity, capacitance and a resistance, as illustrated in FIG. 7. The transmission property over time is calculated by the method of characteristics.

The pump 2 in the simulation model generates a discontinuous flow Q(t). A peristaltic pump in which a maximum rotational speed n=600 l/min can generate a maximum flow Q of 60 ml/min is assumed. The pump wheel is assumed to have seven rollers 3. Hence, the maximum excitation frequency of the rotating pump rollers 3 is $$f_{max} = \frac{600}{60 \text{ s}} \cdot 7 = 70 \text{ Hz}.$$

The peristaltic pump 2 is coupled to the simulation network as a boundary condition and delivers a volume flow from the aspiration region according to the following law:

$$Q(t) = \frac{\pi}{600} \cdot 60 \text{ ml} \cdot (1 + 1/4 \cdot \sin(7 \cdot \pi/30 \cdot n \cdot t)).$$

FIGS. 16 to 19 show tables which present the input data for the hydraulic simulation. The characteristic variables and the hydraulic properties are in this case illustrated per element. The system is tuned as follows: The flow of the peristaltic pump 2 is increased linearly from 0 to 600 l/min over a period from t=0 to 240 seconds, which corresponds to 0 to 60 ml/min, and it subsequently remains constant at the final value. The flow pulse excitation from 0 to 70 Hz is effected in an analogous fashion.

Figure 10:
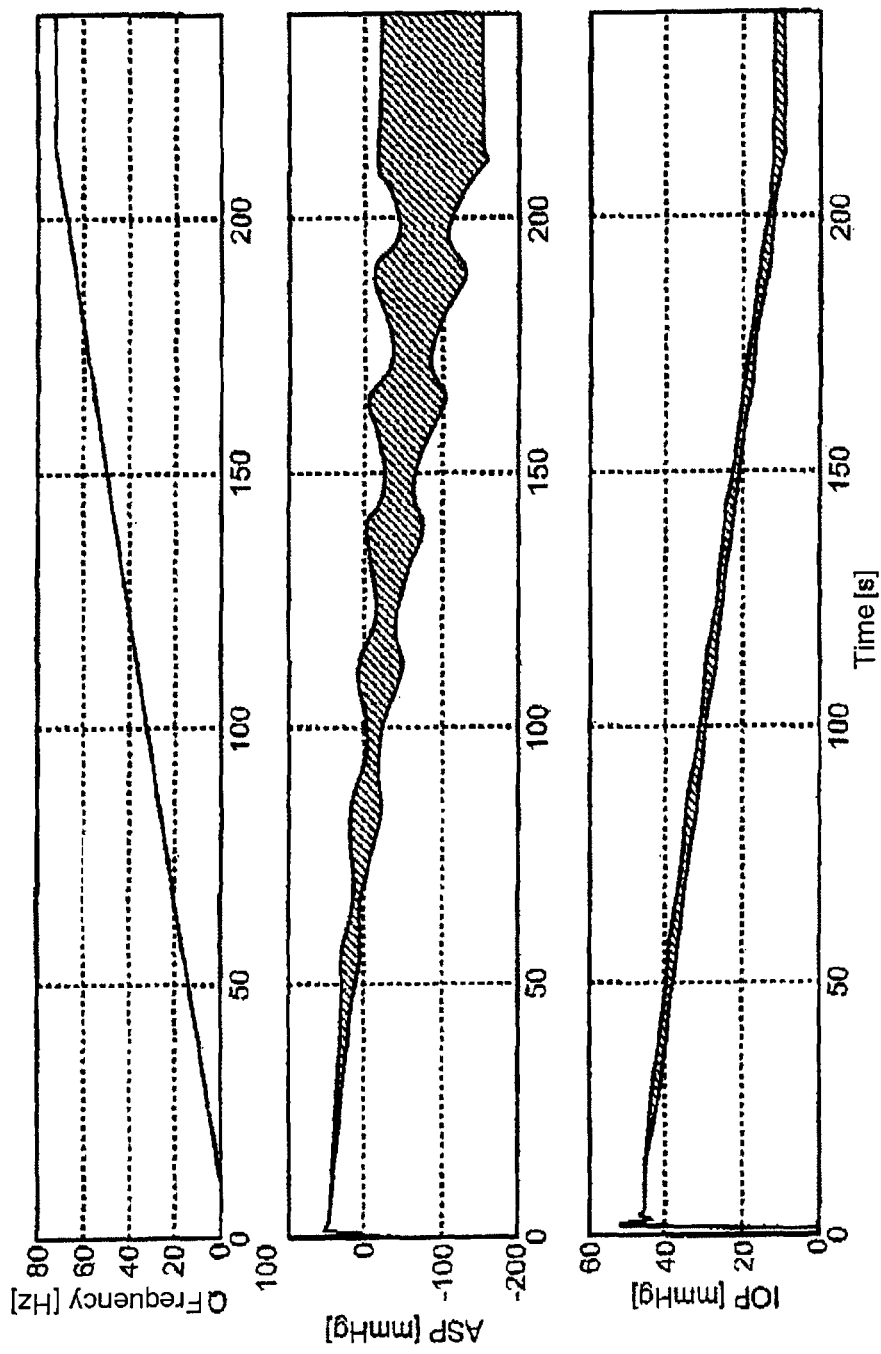
FIG. 10 shows diagrams which show the rotational frequencies of the pump, the amplitudes of the pressure wave and the internal eye pressure as a function of time at a ratio of K=1.
Figure 11:
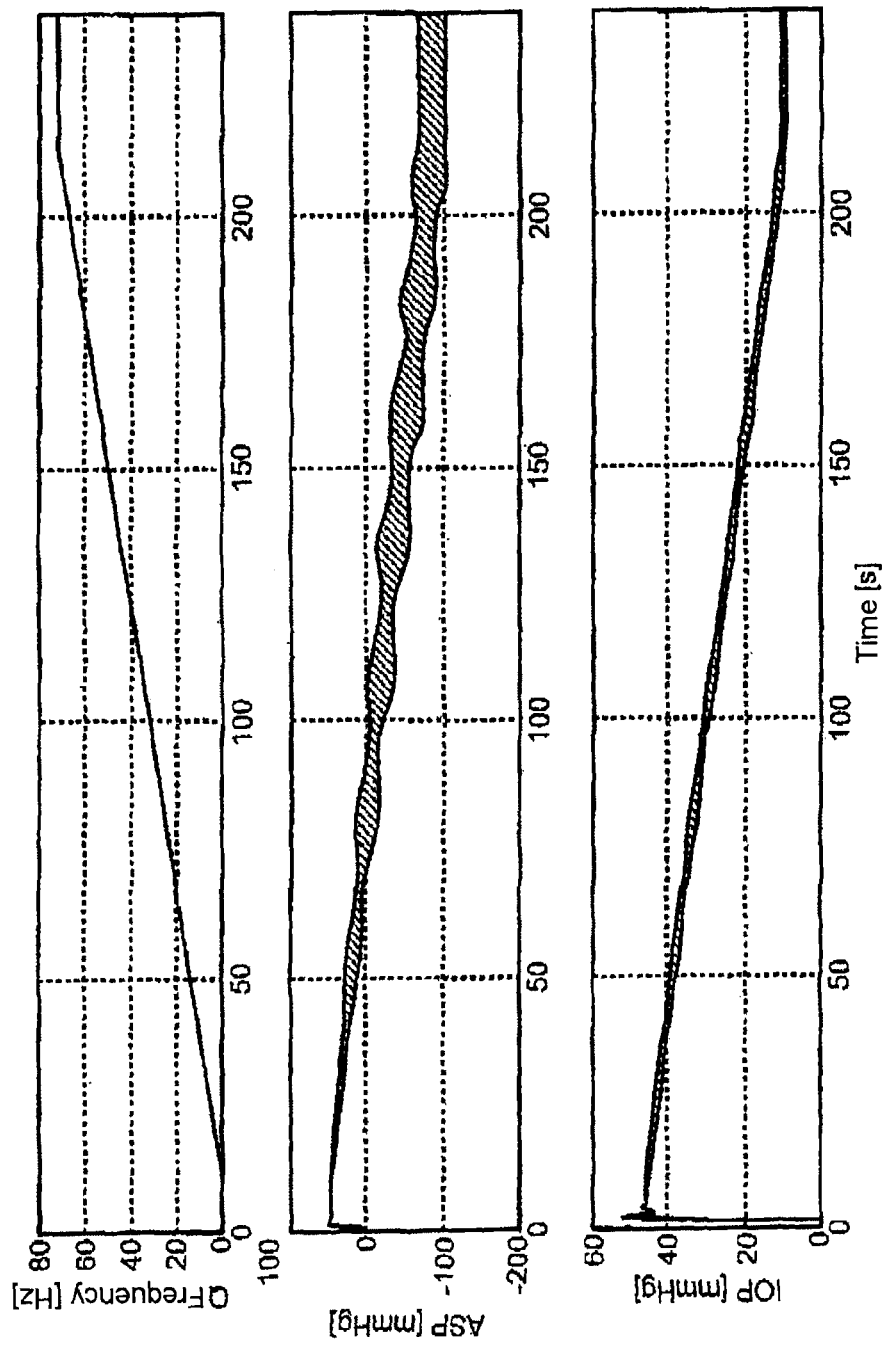
FIG. 11 shows diagrams which show the rotational frequencies of the pump, the amplitudes of the pressure wave and the internal eye pressure as a function of time at a ratio of K=15.
Figure 12:
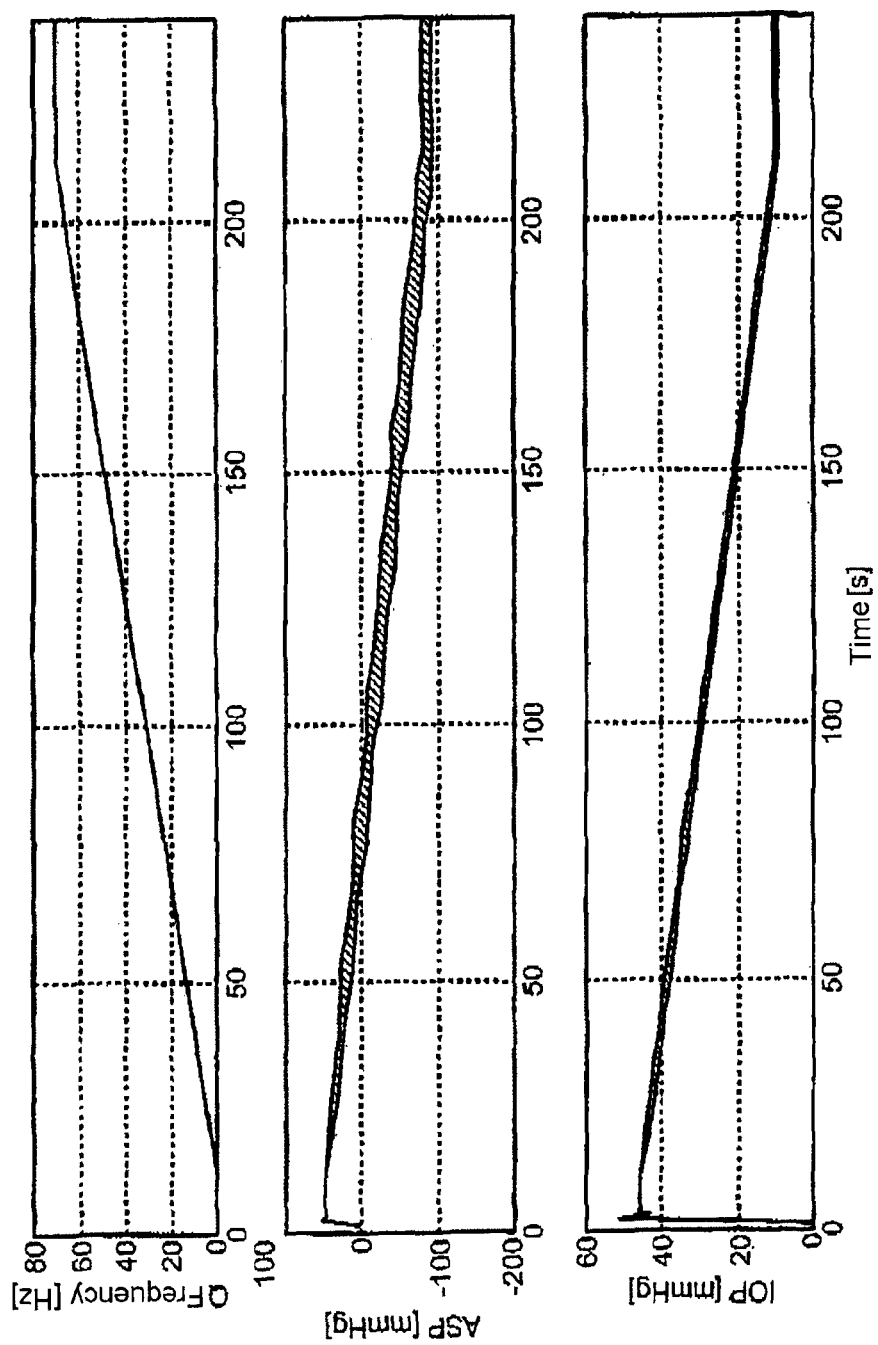
FIG. 12 shows diagrams which show the rotational frequencies of the pump, the amplitudes of the pressure wave and the internal eye pressure as a function of time at a ratio of K=20.
Figure 13:
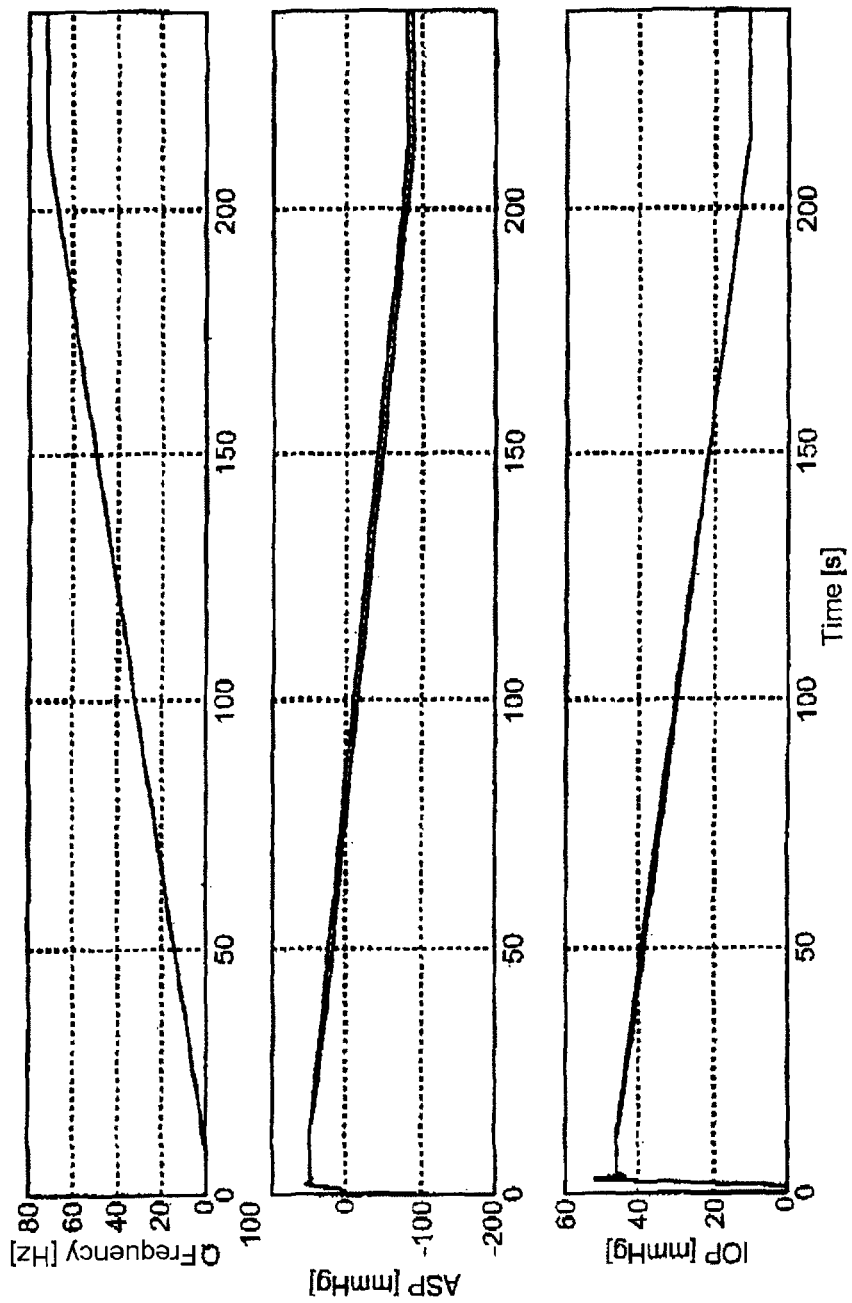
FIG. 13 shows diagrams which show the rotational frequencies of the pump, the amplitudes of the pressure wave and the internal eye pressure as a function of time at a ratio of K=30.

In FIG. 10, the upper curve shows the pump rotational speed or the frequency of the volume flow pulses Q(t) with a continuous constant increase up to the maximum rotational speed of n=600 l/min, corresponding to f=10*7=70 Hz. The pressure pulsation curve (ASP) illustrated therebelow shows the pressure oscillations on the pump side in the aspiration branch. Obvious resonances where there are significantly stronger pressure pulsations can be seen at certain frequencies. The reason for this is that the pressure waves in the elastic line system propagate at a speed of approximately 40.8 m/s and a standing wave can be formed at certain frequencies by the reflective behavior due to the boundary conditions. In the case of one oscillation antinode and one oscillation node in an elastic aspiration line (l=2 m, c=40.8 m/s), the first fundamental frequency can be determined according to the following laws:

$\lambda_0 = 4 \cdot l,$ $f_0 = c/\lambda_0.$

The subsequent higher resonant frequencies of the standing waves are determined by multiplying the fundamental resonant frequency $f_0$ with increasing odd numbers:

$\lambda_1 = 4/3 \cdot l,$ $f_1 = c/\lambda_1,$ and $\lambda_2 = 4/5 \cdot l,$ $f_2 = c/\lambda_2,$ etc.

Hence, with l=2 m, c=40.8 m/s, the resonant frequencies can be determined as:

$f_0$=5.1 Hz, $f_1$=15.3 Hz, $f_2$=25.5 Hz, etc. These resonant frequencies of the standing waves in the elastic line system can clearly be seen in the aspiration pressure profile shown in FIG. 10. The continuous tuning of the excitation frequency of the peristaltic pump 2 clearly shows the response behavior of the elastic aspiration line in respect of the estimated, resonant standing natural oscillations. The third diagram in FIG. 10 shows the pressure oscillations (intraocular pressure IOP) transmitted to the eye II from the pressure pulsations in the aspiration line as a function of time.

The resonant frequencies derived from the fundamental estimations can clearly be seen in FIG. 10.

The invention ensures that the pressure pulsations in the eye excited by the standing waves in the aspiration line system are damped, or an impedance transformation is performed, and so no additional capacitance is inserted into the aspiration branch and so it is not necessary to reduce the line cross section within the aspiration branch.

According to the invention, this is effected by the device comprising a diffuser arrangement 9 upstream of the pump 2 and downstream of the handpiece 6. This diffuser arrangement 9 is designed such that it transforms the natural frequency regions of the standing waves in the aspiration branch 4 such that the pressure pulsation excitations no longer reach the chamber of the eye. FIG. 8 illustrates a model of the partial system of the surgical system I on which the simulation calculation is based. In contrast to FIG. 6, the part 26 is in this case replaced by the diffuser arrangement 9. FIG. 9 indicates that for the flow-technical modeling, a replacement circuit diagram of capacitors, inductors and resistors can likewise be used for the diffuser arrangement 9, which replacement circuit diagram can be designed in an individual fashion for the simulation.

In accordance with the explanation described above, the diffuser element or elements of a diffuser arrangement 9 comprise a small internal dimension D1 and a large internal dimension D2. The ratio K of the internal dimensions is referred to as the opening factor:

$K = D2/D1.$

In the exemplary embodiment, the length L of the diffuser arrangement 9 should be approximately 5% of the length of the elastic aspiration tube (ASP tube), that is to say approximately L=100 mm in the case of an aspiration tube with a length of 2 m.

In accordance with the model according to FIG. 8, a simulation is performed with a diffuser model. The diffuser is included in the model in the form of a discretization according to FIG. 4f with equidistant diameter steps and it comprises ten partial segments DIFF1 to DIFF10.

The diffuser arrangement 9 has the identical wall thickness h and length and the same plastic material as the part 26 of the cylindrical aspiration line in the cassette 20 in the model according to the prior art, as in FIG. 6. Hence, the model according to the prior art has a tube with an opening factor of K=1 if the above definition is to be used as the basis of a diffuser. Here, an identical simulation procedure to the model according to the prior art is assumed, with the parameters for the simulation of the prior-art model being illustrated in the table in accordance with FIG. 16.

It is the opening factor K of the diffuser in particular which is optimized for determining the optimum design of the diffuser arrangement 9.

Here, polycarbonate is considered for the material of the aspiration line in the cassette 20 or for the diffuser, and it can be used as a cost-effective injection-molding material. By way of example, the Young's modulus is assumed to be 2 GPa.

Figure 14:
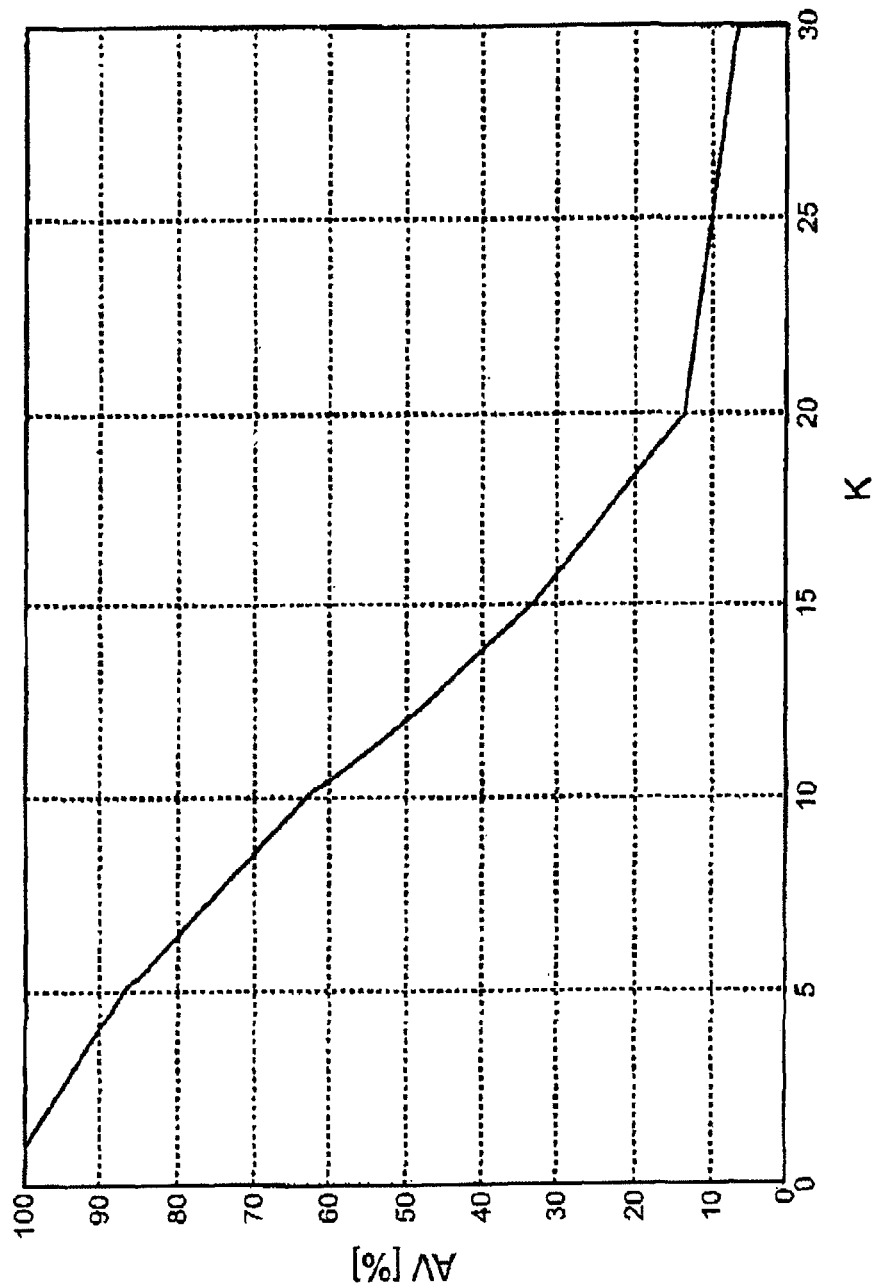
FIG. 14 shows a diagram in which a percentage amplitude ratio of the pressure wave is illustrated as a function of the ratio K.

It was found that, in accordance with FIG. 14, the transmission and resonance properties in the aspiration branch 4 are significantly changed in the case of an opening factor of K>1. FIG. 14 illustrates, in percent, the ratio AV of the oscillation amplitudes at the respective value of K>1 in respect of the oscillation amplitude at K=1, wherein $$AV = \frac{A_{K=x}}{A_{K=1}}$$

holds true. From an opening factor of K>10 to K=30, there is a significant reduction in the oscillation amplitudes. The tables in FIGS. 17 to 19 show, for the cases K=15, K=20, K=30, the parameters of the optimized diffuser element, with the respective diffuser increments DIFF1 to DIFF10 in accordance with FIG. 4f, on which the simulation is based.

The diagrams in FIGS. 10 to 13 show the initial simulation profile for K=1, K=15, K=20 and K=30. While the natural frequencies remain almost unchanged, the amplitudes of the intraocular pressure IOP and the aspiration pressure decrease with increasing K. Almost no pulsations can be detected anymore in the eye II in the case of high K.

The smaller internal dimension D1 preferably equals the internal dimension of the elastic aspiration tube.

In the case of a corresponding design using simulation software such as Matlab/Simulink or, for example, 3D multiphysics tools such as Comsol, the use of diffuser elements in the aspiration branch 4 leads to an optimized design of the diffuser arrangement 9.

The pulse transmission function of the aspiration branch 4, in conjunction with the use of a peristaltic pump 2 and an elastic aspiration tube system, can be designed such that the pressure pulsations of a peristaltic pump 2 can be reduced significantly without additional capacitors having to be inserted in the aspiration region or without the internal cross section of the suction line having to be reduced significantly.

Figure 15:
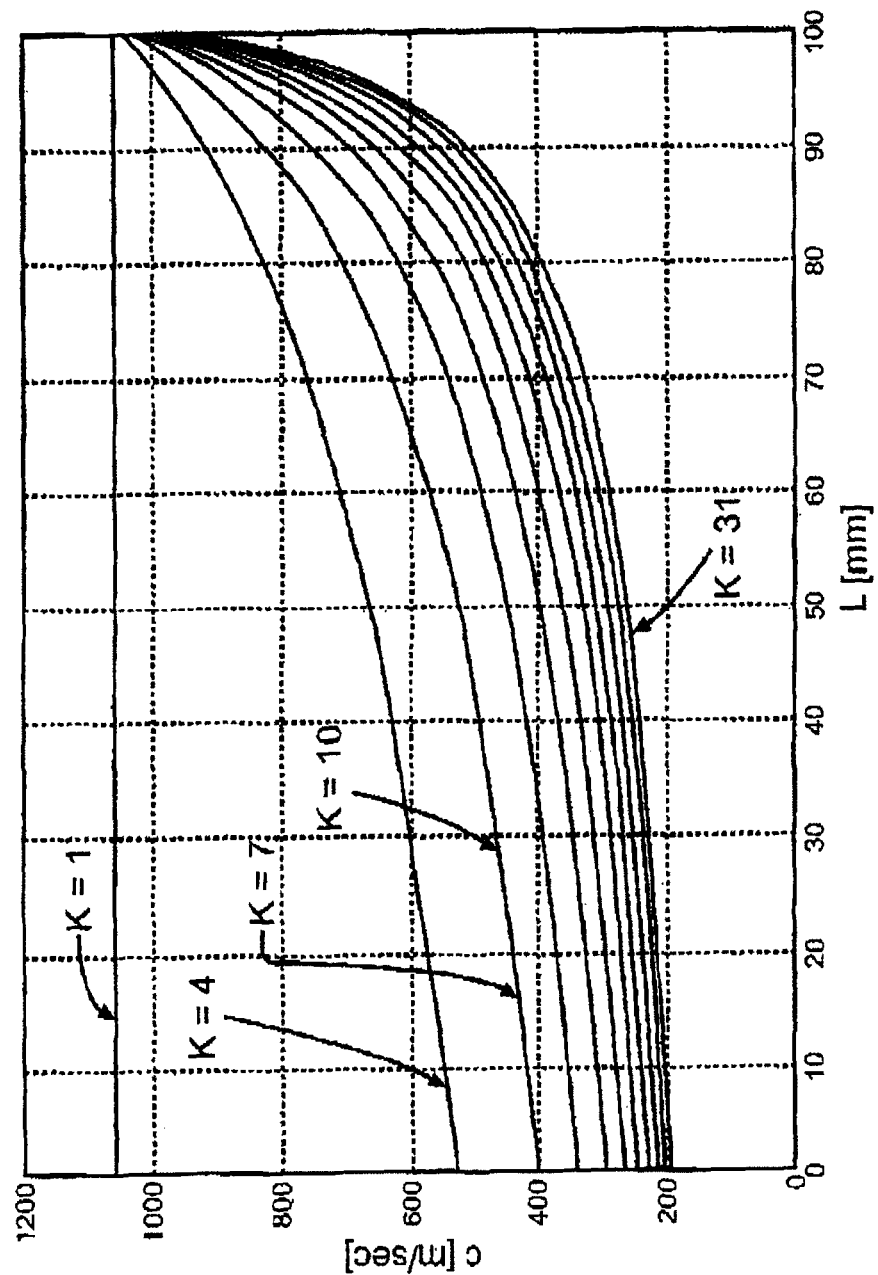
FIG. 15 shows a diagram in which the wave propagation speed is illustrated as a function of the length of the diffuser arrangement for different values of the ratio K.

FIG. 15 shows the profile of the phase speed c along the longitudinal axis of a diffuser arrangement 9 over the length L thereof, wherein the fluid, analogously, for example, to the arrangements in FIGS. 2 and 8, is supplied from the right-hand side and leaves the diffuser arrangement 9 on the left-hand side in the direction of the pump 2. Hence, the value 0 in FIG. 15 is at the larger internal dimension D2 and the value 100 is at the smaller internal dimension D1.

No change in the phase speed c can be detected along the longitudinal axis for K=1. At higher values of K, the phase speed c is reduced along the longitudinal axis with increasing diffuser length L, starting from the smaller internal dimension D1 and toward the larger internal dimension D2. FIG. 15 shows characteristic lines for different values of K from K=1 to K=31.

The mentioned optimization properties: cross section, bore, length and, in particular, the opening factor K are preferably optimized for the corresponding application using a 3D multiphysics tool such as Comsol multiphysics.

In accordance with the tables in FIGS. 17 to 19, only the variable K was used as a variable in the above-described simulation for determining the design of a diffuser arrangement 9 and the other mentioned variables such as BSS tube etc. were based on fixed parameters with the values mentioned in an exemplary fashion. Since the variable K has the most significant influence in respect of damping the amplitude of the pressure wave, the optimization thereof is paramount. However, for a further improvement, provision can also be made for the variables BSS tube and/or IRR tube and/or IRR handpiece and/or ASP handpiece and/or EYE R and/or EYE C and/or ASP tube and/or ASP line to be based on different fixed values or even be defined as variables in the simulation run. However, reference should be made to the fact that these mentioned variables have a significantly lower influence on the damping of the amplitude of the pressure waves than the variable K; in specific conditions they also have a negligible influence.

The invention claimed is:

1. A device, comprising:
 a diffuser arrangement configured to be arranged in an aspiration branch of a surgical system so that the diffuser arrangement reduces pressure variations of a fluid flowing in the aspiration branch,
 wherein:
  the pressure variations are generated by a pump delivering the fluid into the aspiration branch in a discontinuous fashion;
  the device is upstream of the pump in a flow direction of the fluid in the aspiration branch;
  the diffuser arrangement comprises at least two diffusers;
  the diffuser arrangement has a ratio between its maximum internal dimension and its minimum internal dimension;
  the ratio is greater than or equal to 2; and
  when the diffuser arrangement is connected to the aspiration branch, the at least two diffusers are arranged in parallel along the flow direction.

2. The device as claimed in claim 1, wherein the diffuser arrangement is detachably arranged in the aspiration branch.

3. The device as claimed in claim 1, wherein a minimum internal dimension of a region of the diffuser arrangement through which fluid flows is greater than or equal to a minimum internal dimension of a front opening of a hollow needle of a surgical handpiece that can be connected to the aspiration branch.

4. The device as claimed in claim 3, wherein the minimum internal dimension of the diffuser arrangement is between 0.8 mm and 2.5 mm.

5. The device as claimed in claim 3, wherein a maximum internal dimension of the region of the diffuser arrangement through which fluid flows is between 1.2 mm and 25 mm.

6. The device as claimed in claim 1, wherein the diffuser arrangement is connected to an elastic aspiration tube of the aspiration branch, and a length of the diffuser arrangement is less than 15% of a length of the aspiration tube.

7. The device as claimed in claim 1, wherein the diffuser arrangement has a length of between 10 mm and 400 mm.

8. The device as claimed in claim 1, wherein the diffuser arrangement is configured to be arranged in a fluidics cassette.

9. The device as claimed in claim 1, wherein the diffuser arrangement has its minimum internal dimension at the first opening of the first diffuser, and the diffuser arrangement has its maximum internal dimension at the second opening of the first diffuser.

10. The device as claimed in claim 1, wherein the at least two diffusers comprise a first diffuser, and the first diffuser has a continuously increasing internal dimension over its length.

11. The device as claimed in claim 1, wherein the at least two diffusers comprise a first diffuser, and the first diffuser has an inner side having an at least partially curved design in a longitudinal direction of the diffuser.

12. The device as claimed in claim 1, wherein the at least two diffusers comprise a first diffuser, and the first diffuser has an inner side having an at least partially stepped design in a longitudinal direction of the diffuser.

13. The device of claim 1, wherein the surgical system is an ophthalmic microsurgical system for lens surgery.

14. The device as claimed in claim 1, wherein:
the at least two diffusers comprise a first diffuser;
the first diffuser comprises a wall defining a first opening and a second opening;
the second opening of the first diffuser is separated from the first opening of the first diffuser by the wall; and
when the diffuser arrangement is connected to the aspiration branch, the first opening of the first diffuser is upstream of the second opening of the first diffuser in the flow direction.

15. A device, comprising:
a diffuser arrangement configured to be arranged in an aspiration branch of a surgical system so that the diffuser arrangement reduces pressure variations of a fluid flowing in the aspiration branch,
wherein:
    the pressure variations are generated by a pump delivering the fluid into the aspiration branch in a discontinuous fashion;
    the device is upstream of the pump in a flow direction of the fluid in the aspiration branch;
    the diffuser arrangement comprises at least two diffusers;
    the diffuser arrangement has a ratio between its maximum internal dimension and its minimum internal dimension;
    the ratio is greater than or equal to 2; and
    when the diffuser arrangement is connected to the aspiration branch, the at least two diffusers are arranged in series along the flow direction.

16. A device, comprising:
a diffuser arrangement configured to be arranged in an aspiration branch of a surgical system so that the diffuser arrangement reduces pressure variations of a fluid flowing in the aspiration branch,
wherein:
    the pressure variations are generated by a pump delivering the fluid into the aspiration branch in a discontinuous fashion;
    the device is upstream of the pump in a flow direction of the fluid in the aspiration branch;
    the diffuser arrangement comprises at least two diffusers;
    the diffuser arrangement has a ratio between its maximum internal dimension and its minimum internal dimension;
    the ratio is greater than or equal to 2;
    the at least two diffusers comprise first and second diffusers;
    when the diffuser arrangement is connected to the aspiration branch, the first diffuser is upstream of the second diffuser in the flow direction;
    the second diffuser has a wall defining a first opening and a second opening;
    the second opening of the second diffuser is separated from the first opening of the second diffuser by the wall; and
    when the diffuser arrangement is connected to the aspiration branch, the first opening of the second diffuser is upstream of the second opening of the second diffuser in the flow direction; and
    the first opening of the first diffuser is smaller than the first opening of the second diffuser.

17. A device, comprising:
a diffuser arrangement configured to be arranged in an aspiration branch of a surgical system so that the diffuser arrangement reduces pressure variations of a fluid flowing in the aspiration branch,
wherein:
    the pressure variations are generated by a pump delivering the fluid into the aspiration branch in a discontinuous fashion;
    the device is upstream of the pump in a flow direction of the fluid in the aspiration branch;
    the diffuser arrangement comprises at least two diffusers;
    the diffuser arrangement has a ratio between its maximum internal dimension and its minimum internal dimension;
    the ratio is greater than or equal to 2;
    the at least two diffusers comprise first and second diffusers;
    when the diffuser arrangement is connected to the aspiration branch, the first diffuser is upstream of the second diffuser in the flow direction;
    the second diffuser has a wall defining a first opening and a second opening;
    the second opening of the second diffuser is separated from the first opening of the second diffuser by the wall; and
    when the diffuser arrangement is connected to the aspiration branch, the first opening of the second diffuser is upstream of the second opening of the second diffuser in the flow direction; and
    the first opening of the first diffuser is larger than the second opening of the second diffuser.

* * * * *

UNITED STATES PATENT AND TRADEMARK OFFICE
CERTIFICATE OF CORRECTION

| | | |
|---|---|---|
| PATENT NO. | : 8,801,666 B2 | Page 1 of 1 |
| APPLICATION NO. | : 12/666007 | |
| DATED | : August 12, 2014 | |
| INVENTOR(S) | : Kuebler et al. | |

It is certified that error appears in the above-identified patent and that said Letters Patent is hereby corrected as shown below:

On the Title page, Item [75], Col. 1, line 4, 4$^{th}$ inventor, delete "Stuggart" and insert -- Stuttgart --.

On the Title page, Item [56], Col. 2, line 1, delete "Intoduction" and insert -- Introduction --.

In the Specification

Col. 8, line 32, delete "which" and insert -- 9 which --.

Col. 9, line 40, delete "are" and insert -- 23 are --.

Col. 10, line 42, delete "in" and insert -- 22 in --.

Col. 13, line 64, delete "$C_h$," and insert -- $C_h$ --.

Signed and Sealed this

Eighteenth Day of November, 2014

Michelle K. Lee
*Deputy Director of the United States Patent and Trademark Office*